United States Patent
Natrajan et al.

(10) Patent No.: US 6,664,043 B2
(45) Date of Patent: Dec. 16, 2003

(54) ACRIDINIUM ESTER LABELS HAVING HYDROPHILIC MODIFIERS

(75) Inventors: Anand Natrajan, Manchester, NH (US); David Sharpe, Foxborough, MA (US); Qingping Jiang, Northborough, MA (US)

(73) Assignee: Bayer Corporation, Tarrytown, NY (US)

( * ) Notice: Subject to any disclaimer, the term of this patent is extended or adjusted under 35 U.S.C. 154(b) by 50 days.

(21) Appl. No.: 09/898,381

(22) Filed: Jul. 3, 2001

(65) Prior Publication Data
US 2003/0045716 A1 Mar. 6, 2003

(51) Int. Cl.[7] .................. C12Q 1/00; C07D 219/04; C07D 475/04
(52) U.S. Cl. ................ 435/5; 435/6; 435/7.1; 435/7.5; 530/391.5; 536/18.7; 544/257; 544/268; 546/104
(58) Field of Search .............. 546/104; 536/18.7; 435/5, 6, 7.1, 7.5; 530/391.5; 544/257, 268

(56) References Cited

U.S. PATENT DOCUMENTS 5,656,426 A * 8/1997 Law et al. ............ 435/6

* cited by examiner

*Primary Examiner*—Bernard Dentz
(74) *Attorney, Agent, or Firm*—Andrew L. Klawitter; John M. Paolino

(57) ABSTRACT

The present invention is generally directed to detectable chemiluminescent acridinium ester labels having hydrophilic modifiers; to compositions, complexes and/or conjugates which include such labels; and to processes for performing bioanalytical assays for target analytes which use such labels. Assays for folate, theophylline, and tobramycin (using such labels with hydrophilic modifiers such as nonionic polyethylene glycol and polyionic spermine disulfonate and polyionic spermine dicarboxylate) are described in detail.

25 Claims, 10 Drawing Sheets

ACRIDINIUM ESTER LABELS HAVING HYDROPHILIC MODIFIERS

FIELD OF THE INVENTION

The present invention is useful in bioanalytical applications and is generally directed to detectable chemiluminescent acridinium ester labels having hydrophilic modifiers; to compositions, complexes and/or conjugates which include such labels; and to processes for performing bioanalytical assays for target analytes which use such labels.

BACKGROUND OF THE INVENTION

Acridinium esters are extremely useful chemiluminescent labels that have been extensively used in the field of immunoassays as well as nucleic acid assays. Each of the following patent documents is both (a) incorporated herein by reference in its respective entirety; and (b) directed to varying aspects of bioanalytical applications of acridinium ester compounds. EP0263657; U.S. Pat. No. 4,745,181; EP0353971; EP0361817; U.S. Pat. No. 4,918,192; U.S. Pat. No. 5,110,932; U.S. Pat. No. 5,227,489; U.S. Pat. No. 5,241,070; EP0617288; WO9421823; U.S. Pat. No. 5,395,752; EP0661270; U.S. Pat. No. 5,449,556; WO9527702; U.S. Pat. No. 5,538,901; U.S. Pat. No. 5,595,875; EP0754178; U.S. Pat. No. 5,656,426; U.S. Pat. No. 5,656,500; U.S. Pat. No. 5,663,074; U.S. Pat. No. 5,702,887; WO9854574; U.S. Pat. No. 5,879,894; WO9911813; WO0009487; EP0982298; EP0988551; WO0031543; EP1009852; U.S. Pat. No. 6,080,591; EP1049933; U.S. Pat. No. 6,165,800; WO0109372 & EP1104405. Certain particular detectable chemiluminescent acridinium ester labels lacking hydrophilic modifiers are well-known in the art—e.g., 2',6'-dimethyl-4'-[N-succinimidyloxycarbonyl]phenyl-10-methyl-9-acridine carboxylate and 2',6'-dimethyl-4'-[N-succinimidyloxycarbonyl]phenyl-10-sulfopropyl-9-acridine carboxylate {each label being hereinafter referred to as, respectively, "DMAE-NHS" and "NSP-DMAE-NHS"}—and are being commercialized for immunoassay instrument systems available from Bayer Corporation, Business Group Diagnostics, 511 Benedict Avenue, Tarrytown, N.Y. 10591-5097. For the reader's convenience, the structure of each of these compounds is depicted below.

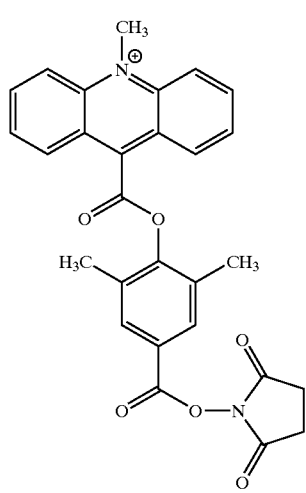

DMAE-NHS

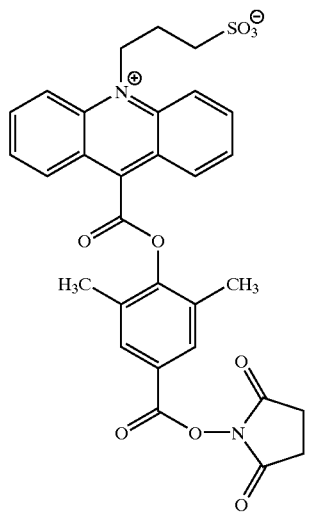

NSP-DMAE-NHS

DETAILED DESCRIPTION OF THE INVENTION

Figure 1:
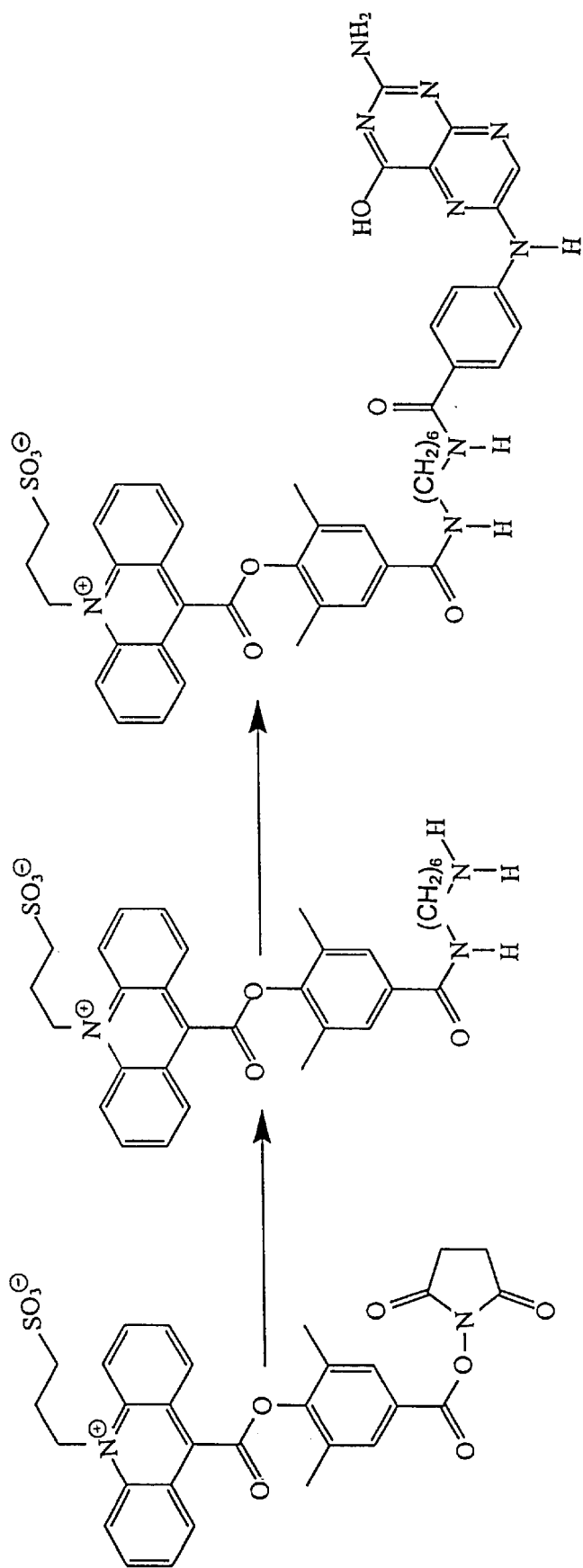
FIG. 1 depicts the synthesis of NSP-DMAE-HD-pteroate.

As previously stated, the present invention is widely directed to detectable chemiluminescent acridinium ester labels having hydrophilic modifiers. In several preferred embodiments of the inventive labels, we have incorporated two (2) types of structural elements in NSP-DMAE and we have found that these modifications allow for the preparation of unique hapten tracers which show enhanced performance in immunoassays. By employing three (3) different clinically relevant analytes—namely—(the vitamin folate, the asthma drug theophylline, and the aminoglycoside antibiotic tobramycin) we have demonstrated the generality of our findings.

Before examining in depth the present inventive labels, a brief overview of assay formats is presented below. Competitive immunoassays commonly: (a) employ a format where a conjugate of a fluorescent or chemiluminescent label to an analyte of interest is used as a tracer in the assay;

and (b) utilizes a solid support. A typical architecture for such a competitive assay consists of three components—namely—a tracer, a sample containing the analyte of interest, and a method for the separation of bound and unbound analyte. (Note that in homogenous immunoassays, however, no separation is performed). For example, immobilization of folic acid binding protein on a solid support such as paramagnetic particles (hereinafter referred to as "PMP") provides a means for achieving such a separation (magnetic) of free and bound analyte (which analyte in this case would be folic acid). When the tracer is included in the assay, it competes with the analyte from the sample for binding to the immobilized protein. Increased levels of analyte in the assay result in less tracer being bound to the immobilized protein.

As described in detail below (and as further exemplified later) two (2) types of spacers which are particularly useful for the preparation of hapten tracers—(a) nonionic polyethylene glycol; and (b) polyionic spermine disulfonate and polyionic spermine dicarboxylate—have been developed.

Polyethylene glycol (hereinafter referred to as "PEG") is a well known polymer. It is biocompatible, soluble in both aqueous and organic solvents, nontoxic, and nonimmunogenic. In the prior art, it has been extensively used as a modifier of a variety of molecules ranging from small molecular weight drugs to large proteins as well as large aggregates such as liposomes. PEG conjugates of drugs exhibit improved solubility and are longer-lived in the bloodstream. PEG modification of proteins and peptides improves solubility, confers resistance to proteolysis, and reduces immunogenicity. PEG modification of oligonucleotides increases solubility and confers nuclease stability. PEG modification of lipids permits the preparation of PEG-grafted liposomes that are sterically stabilized and display improved blood circulation times. An excellent review of the prior art in the uses of PEG is described by S. Zalipsky in *Bioconjugate Chemistry*, 1995, 6, 150–165 (which is incorporated herein by reference in its entirety). The use of PEG to modify the properties of fluorescent dyes is also described in the prior art. PEG-modified fluorescent porphyrin and phthalocyanine dyes have been shown to exhibit decreased aggregation behavior in aqueous solution as well as diminished non-specific binding to components of human serum such as HSA (Human Serum Albumin). These conjugates also show extended fluorescence decay times (PCT/US91/03424 and PCT/US91/03426). Applications of such conjugates in fluorescence immunoassays and in vivo imaging and in vivo tumor therapy were proposed by the same authors.

Notwithstanding the above uses of PEG, modification of acridinium esters with polyethylene glycol has not been described previously. Likewise, polyionic spacers devised using the polyamine spermine as a scaffold for introducing ionic functional groups have also not been reported. We find that these latter molecules are also extremely useful for modifying acridinium esters. The synthesis and applications of these modified acridinium esters follow.

As mentioned earlier, the vitamin folic acid is a clinically important analyte which is commonly measured using immunoassay techniques. As a closely-related compound, pteroic acid is a simplified, structural variant of folic acid which lacks the glutamate moiety normally found in folic acid. We prepared two (2) different NSP-DMAE conjugates of pteroic acid, one containing a hydrophobic aliphatic (hexamethylene) spacer while the other contained a hydrophilic hexaethylene glycol spacer (see FIGS. 1 & 2). The synthesis of the first tracer was accomplished by reacting NSP-DMAE-NHS with 1,6-hexanediamine (hereinafter, referred to as "HD"). The resulting acridinium ester derivative (hereinafter referred to as "NSP-DMAE-HD") was then condensed with $N^{10}$-trifluoroacetyl pteroic acid followed by removal of the trifluoroacetyl protecting group from the conjugate. To prepare an analogous tracer with a PEG spacer, a short diaminohexaethylene glycol was synthesized from commercially available, hexaethylene glycol. The two hydroxyl groups in hexaethylene glycol were converted to methane sulfonate esters which were subsequently displaced with azide. Reduction of the diazidohexaethylene glycol afforded diaminohexaethylene glcyol which then was condensed with NSP-DMAE-NHS. The resulting acridinium ester derivative (hereinafter referred to as "NSP-DMAE-HEG") was coupled to pteroic acid as discussed above.

Figure 3:
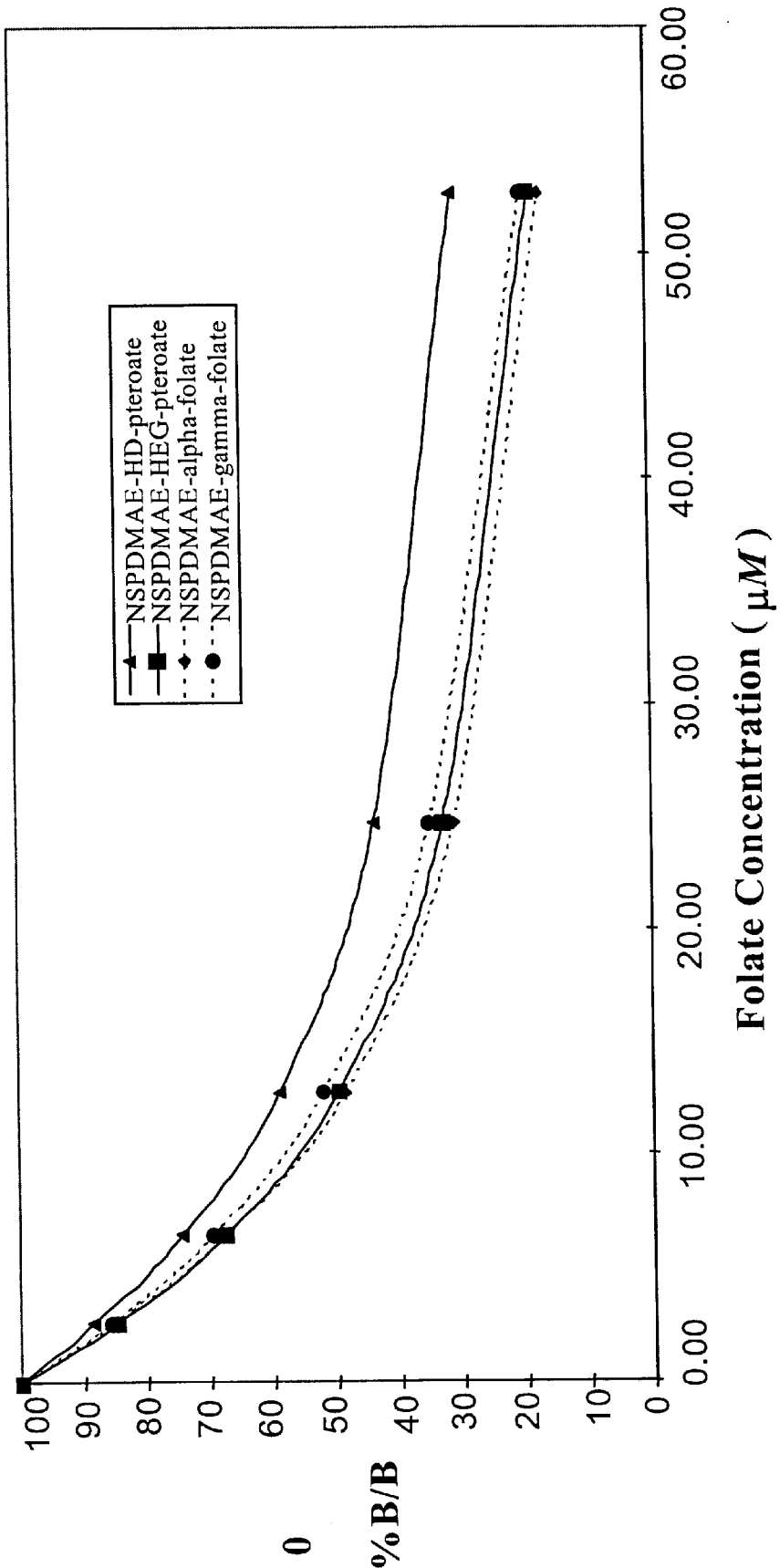
FIG. 3 depicts dose-response curves for DMAE-pteroate conjugates.
Figure 4:
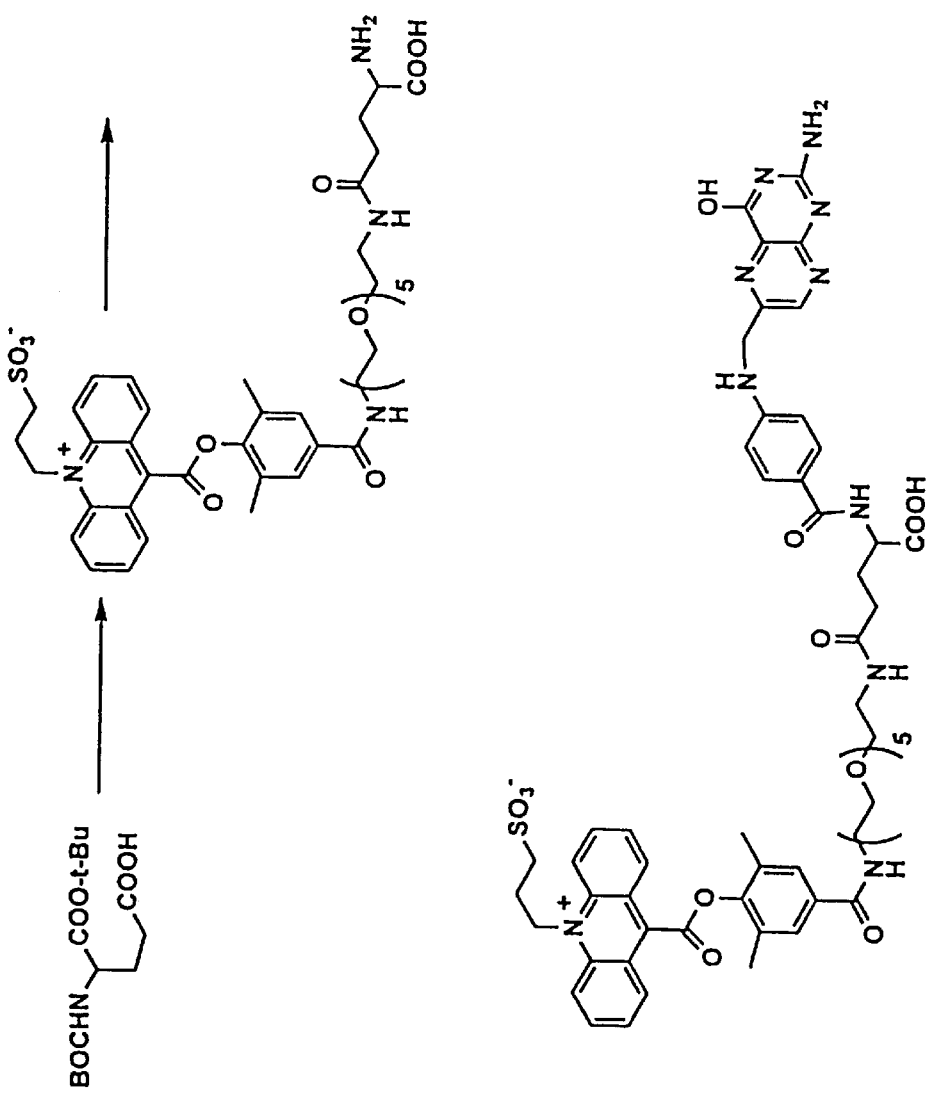
FIG. 4 depicts the synthesis of an NSP-DMAE-folate conjugate with a hexaethylene glycol spacer.
Figure 5:
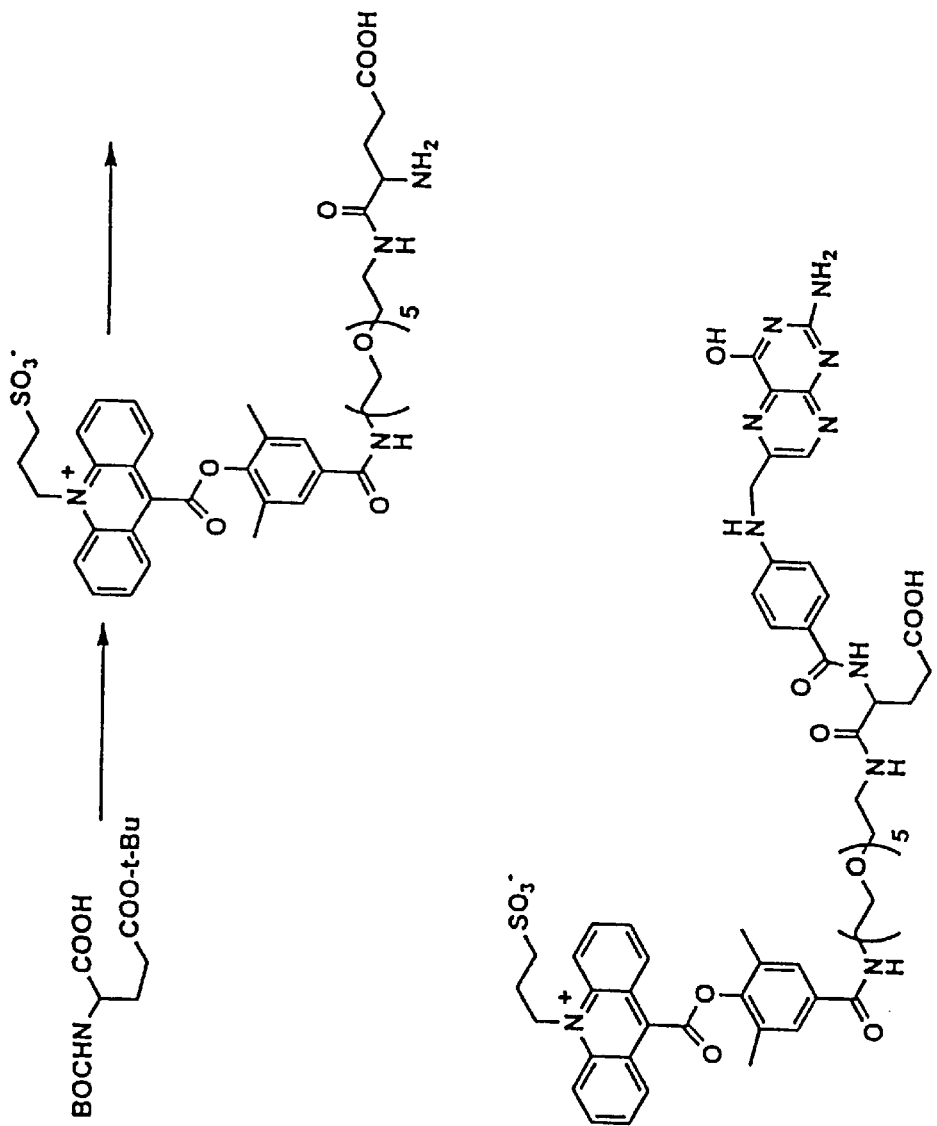
FIG. 5 depicts the synthesis of an alpha-linked folate tracer.

The assay performance of these two (2) different NSP-DMAE-pteroate conjugates was then evaluated in a folate immunoassay (Example 5, Tables 1–3 & FIG. 3). In this assay format, the folate binding protein is immobilized onto PMP and the two (2) tracers compete with the analyte folic acid. The dose-response curves are shown in FIG. 3. The methodology used for generating assay data and the definitions of various assay parameters are explained in Example 5. Tables 1–3 summarize data relating to assay precision, assay accuracy, and assay sensitivity. Incorporation of the hexaethylene glycol spacer between the acridinium ester and pteroate moieties increased tracer binding more than twofold; thus the fraction of bound tracer defined as B/T increased from 0.53% to 1.15% for the tracer with the PEG spacer (Table 3). Clearly, the polyethylene glycol spacer alleviates any steric interference to binding in the PEG-containing tracer. We next synthesized a NSP-DMAE-folate conjugate also containing the hexaethylene glycol spacer (FIG. 4). Since it is known in the prior art that the alpha-carboxylate in folic acid must remain free for good binding to folate binding proteins (Wang, S. et al. *Bioconjugate Chem.* 1996, 7, 56–62), we first synthesized a specific gamma-linked folate tracer. Specifically, this was accomplished by condensing N-tert-butoxycarbonyl glutamic acid alpha-tert-butyl ester with NSP-DMAE-HEG (FIG. 4). Removal of the protecting groups from the resulting conjugate, coupling with $N^{10}$-trifluoroacetyl pteroic acid followed by removal of the trifluoroacetyl group afforded the gamma-linked folate-NSP-DMAE tracer incorporating the short, polyethylene glycol spacer. Evaluation of this tracer in the folate immunoassay, indeed showed even better binding (B/T 1.88%) than the pteroate tracer as would be anticipated. We also prepared a specific alpha-linked folate tracer starting with N-tert-butoxycarbonyl glutamic acid gamma-tert-butyl ester and following the same sequence of reactions described above (FIG. 5). The resulting alpha-linked folate tracer when evaluated in the folate immunoassay exhibited diminished binding owing to the lack of a free alpha-carboxyl group. While there were no discernible differences in assay precision or assay accuracy among the various tracers, the HEG containing tracers did exhibit lower nonspecific binding (Table 3). Thus, NSP-DMAE-HD-pteroate, which does not have a hydrophilic modifier, had the highest nonspecific binding. The analogous HEG containing tracer, which does have a hydrophilic spacer, was >2-fold lower in nonspecific binding. The two (2) folate tracers by virtue of having the hydrophilic HEG spacer had lower nonspecific binding as well. The increased binding combined with the lower nonspecific binding of the HEG containing tracers also increased the dynamic range of the folate assay and improved assay sensitivity (Table 3).

Figure 6:
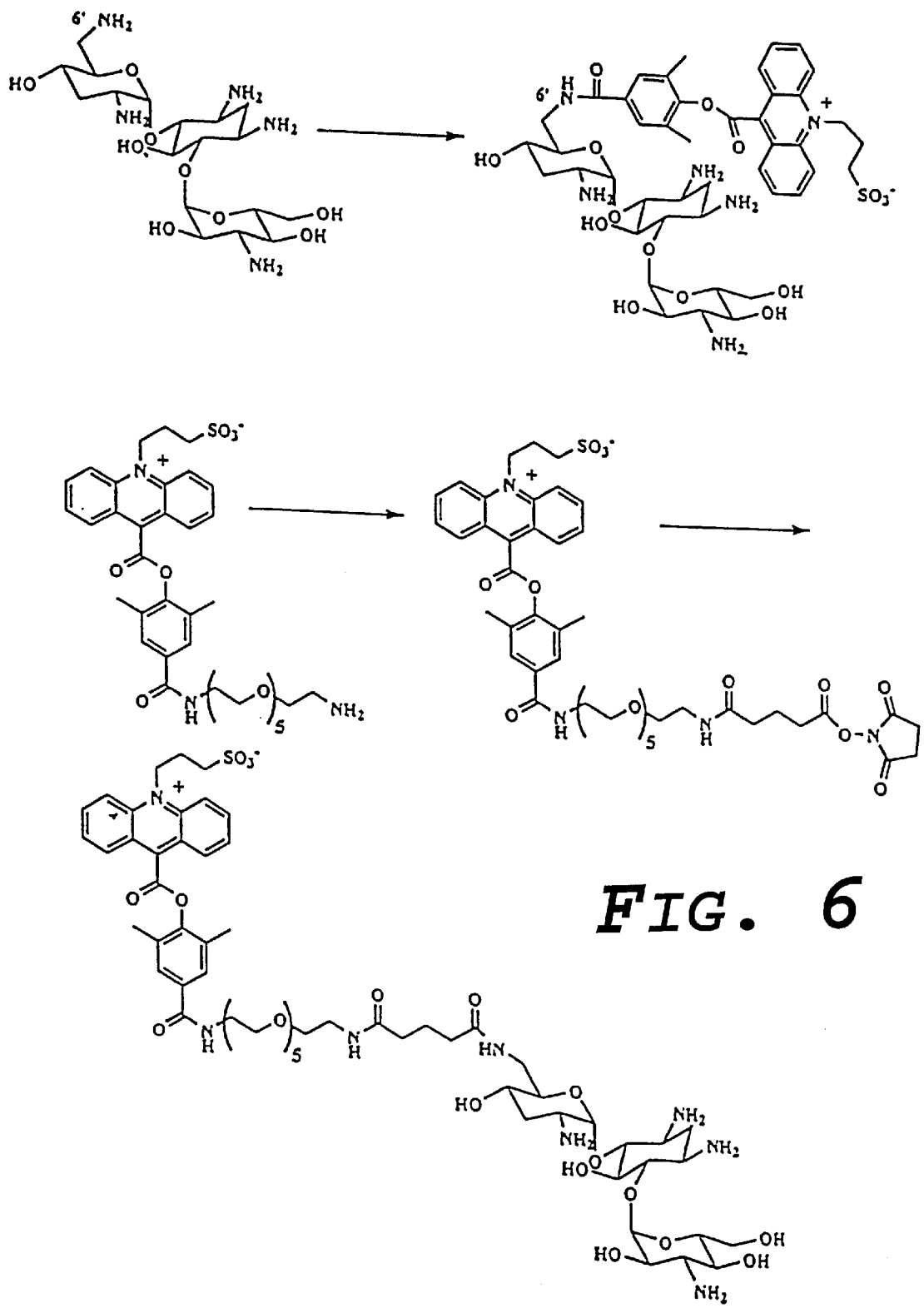
FIG. 6 depicts the synthesis of tobramycin-NSP-DMAE tracers.

In an immunoassay for the aminoglycoside antibiotic tobramycin, we again compared the assay performance of two tobramycin-NSP-DMAE tracers, one of which contained the (hydrophilic) hexaethylene glycol spacer while the other did not. Procedures for generating antibodies for tobramycin as well as for site-specific modification of tobramycin with other small molecules have been described previously (Singh, P. et al. *Can. J. Chem.,* 1984, 62, 2471–2477). In tobramycin, the 6'-amine is the most reactive (FIG. 6). Thus, treatment of the aminoglycoside with one equivalent of NSP-DMAE-NHS furnished a 1:1 tobramycin-NSP-DMAE tracer. The second tracer was prepared by converting NSP-DMAE-HEG to the glutarate derivative by condensation with glutaric anhydride. The carboxylic acid in the resulting adduct (hereinafter referred to as "NSP-DMAE-HEG-glutarate") was then converted to the NHS ester followed by coupling with one equivalent tobramycin to furnish the tracer.

Figure 7:
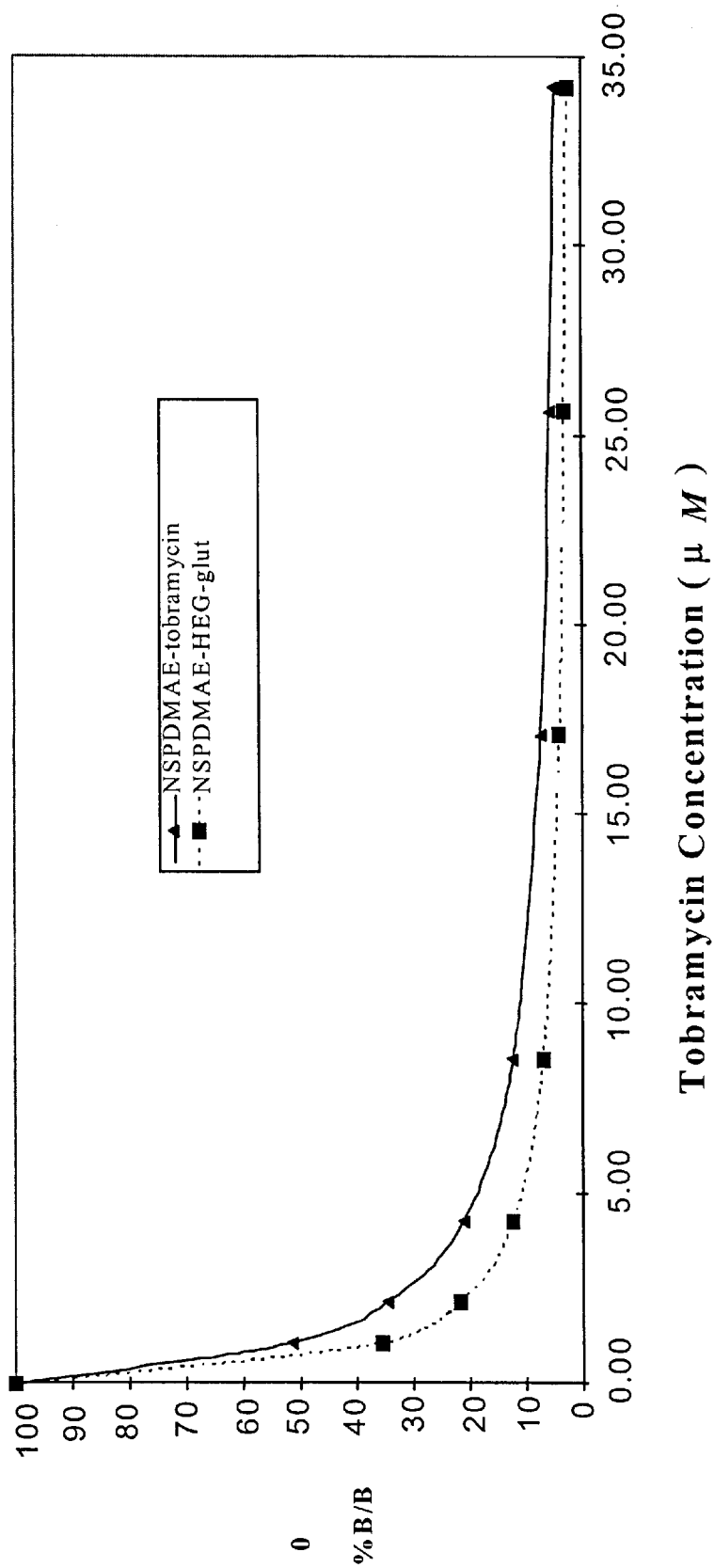
FIG. 7 depicts dose response curves for tobramycin conjugates.

Examination of the two (2) tracers in an immunoassay for tobramycin revealed that while overall binding of the two tracers to a tobramycin antibody on PMP was similar, the nonspecific binding of the hydrophilic PEG-containing tracer was more than 2.5-fold lower than the conventional tracer (Tables 4–6, FIG. 7 in Example 8). Since increased nonspecific binding is most often related to hydrophobicity, it is remarkable that even for a highly, water-soluble analyte such as tobramycin, introduction of the polyethylene glycol modifier in the tracer is so beneficial. While assay precision and assay accuracy was similar for the two (2) tracers, tobramycin assay sensitivity was significantly better (1.7× lower, Table 6) for the HEG containing tracer.

Figure 8:
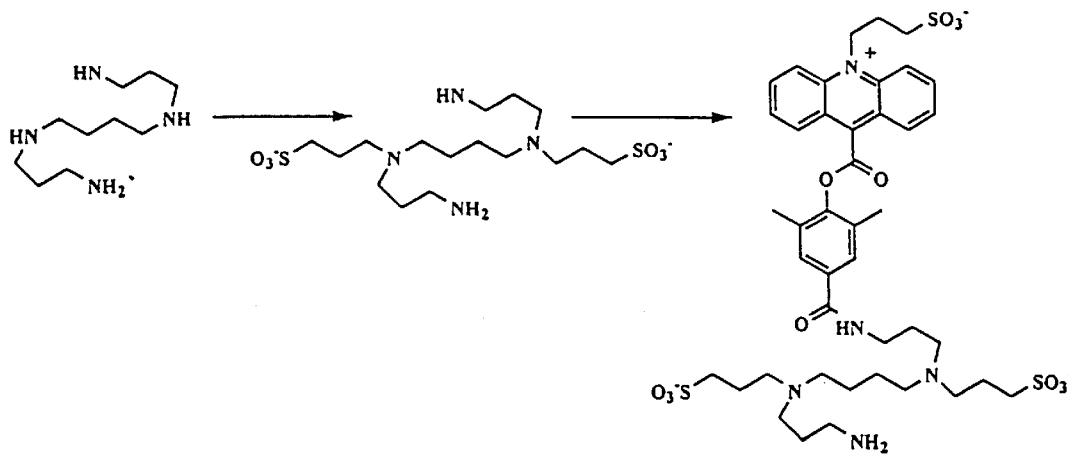
FIG. 8 depicts the synthesis of NSP-DMAE-theophylline tracers.
Figure 8:
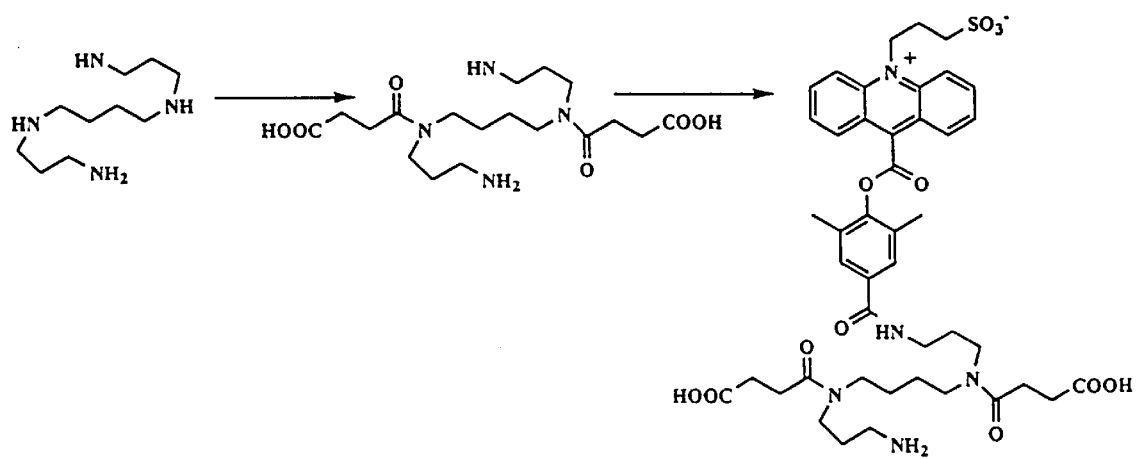
Figure 9:
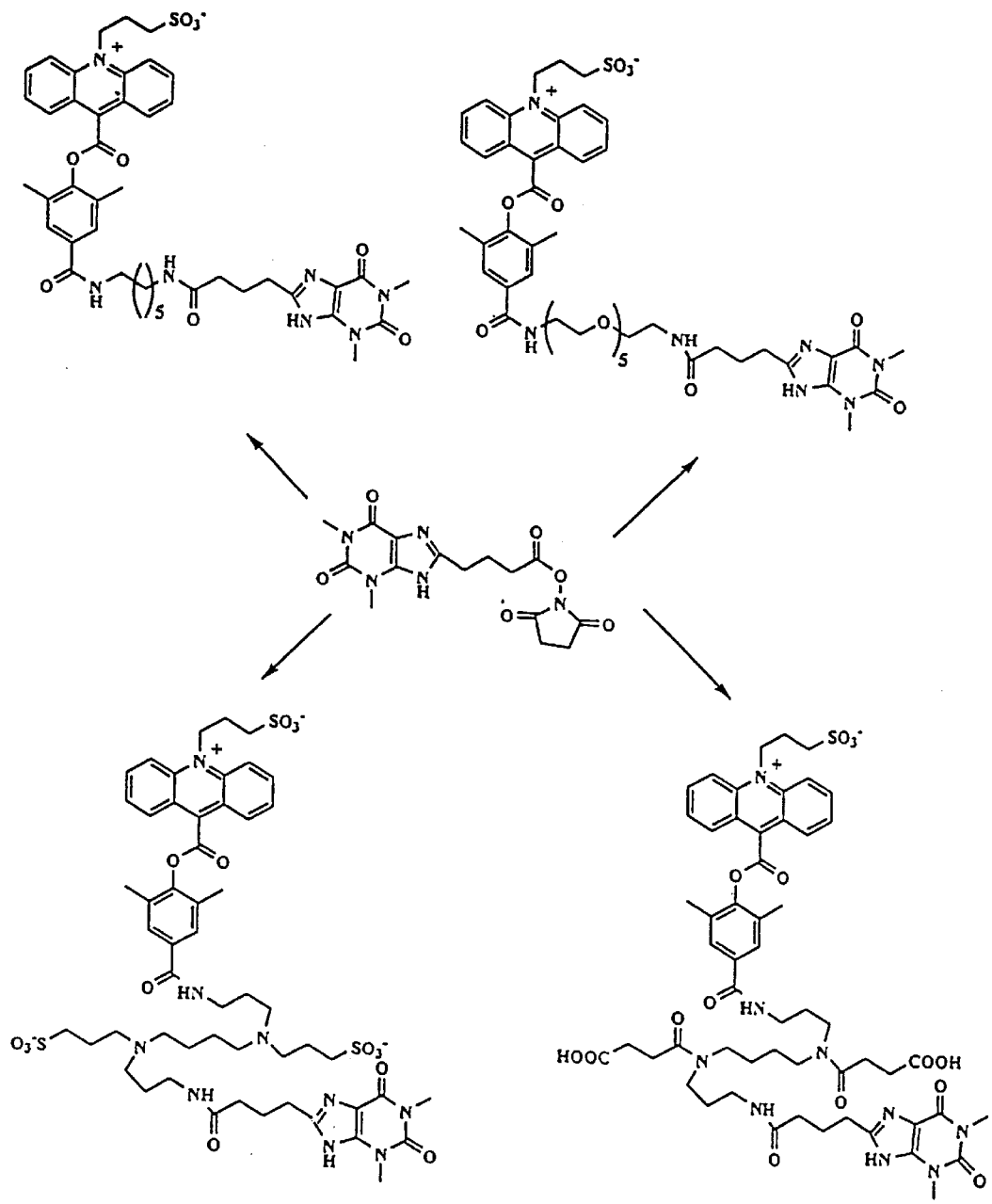
FIG. 9 depicts the coupling of NSP-DMAE derivatives to carboxytheophylline to form tracers.
Figure 10:
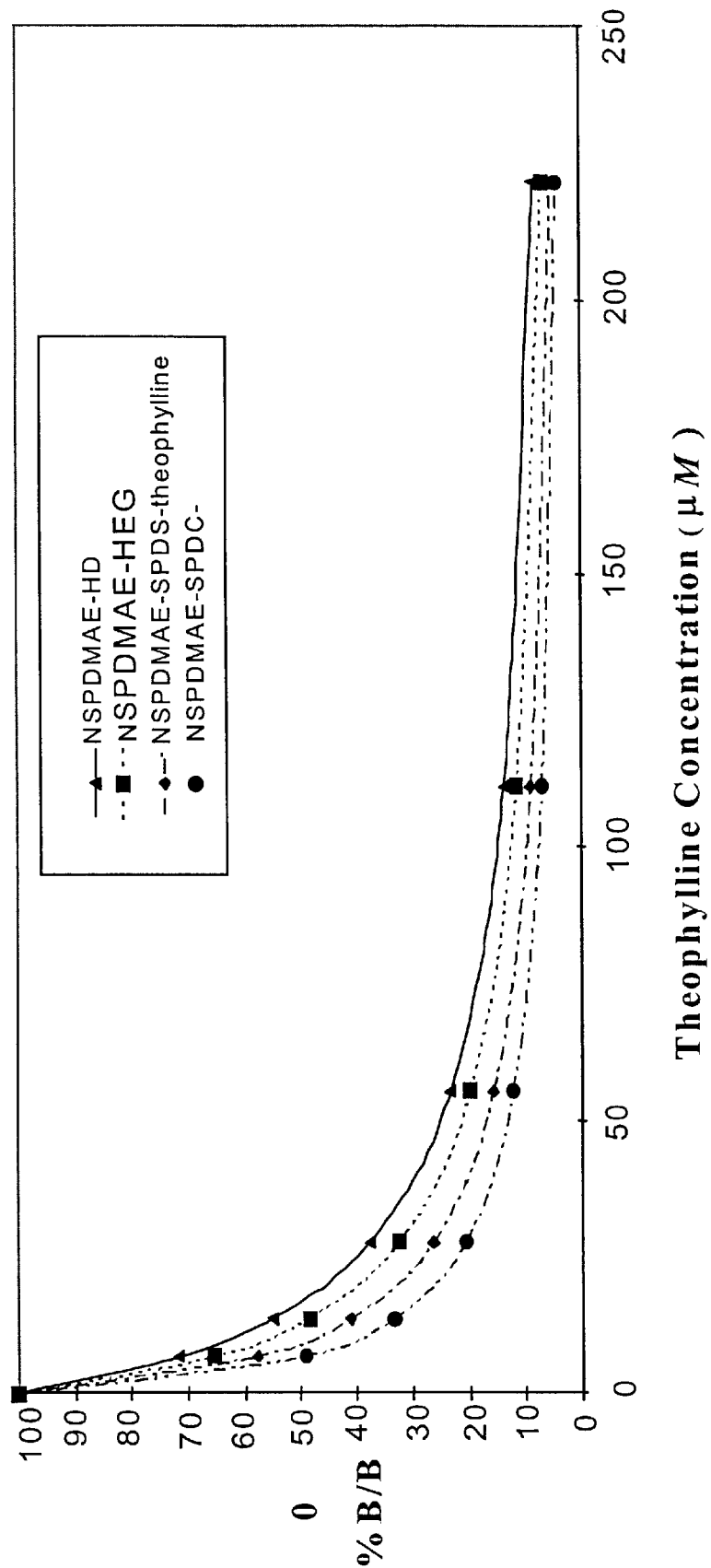
FIG. 10 depicts dose response curves for theophylline conjugates.

In the case of the asthma drug analyte theophylline, in addition to two (2) NSP-DMAE-theophylline tracers incorporating a six-carbon spacer and the hexaethylene glycol spacer (FIGS. 8 & 9) we prepared two (2) new tracers which contain polyionic spacers. The first two (2) tracers were simply prepared by condensing the NHS ester of 8-carboxypropyltheophylline with either NSP-DMAE-HD or NSP-DMAE-HEG. The polyionic spacers were derived from the polyamine, spermine and were prepared by first converting the two primary amines to phthalimido groups. The resulting compound, bis(phthalimido)spermine was either alkylated at the two secondary amines by heating in neat 1,3-propane sultone or acylated with succinic anhydride (FIG. 8). Removal of the phthalimido protecting groups with hydrazine afforded spermine disulfonate (hereinafter referred to as "SPDS") and spermine dicarboxylate (hereinafter referred to as "SPDC"). These new spacers were coupled to NSP-DMAE-NHS and the resulting NSP-DMAE derivatives were coupled to 8-carboxytheophylline (FIG. 9). All four (4) theophylline tracers were then evaluated in a theophylline immunoassay (Example 13, Tables 7–9, FIG. 10). The theophylline tracer containing the hydrophilic PEG spacer showed lower nonspecific binding (2-fold) when compared to the tracer with the nonhydrophilic six-carbon spacer. Tracers containing the SPDS spacer and the SPDC spacer had even lower nonspecific binding (3.7 and 3.1-fold lower than the hydrophobic HD spacer respectively). While binding, assay precision, and assay accuracy was similar for the four (4) tracers, the tracer containing the polycarboxylate spacer SPDC increased assay sensitivity >3-fold. The other hydrophilic spacers did not show such improvement in this specific assay even though both tracers did show lower nonspecific binding.

The above set of results clearly demonstrate the utility of hydrophilic spacers in acridinium ester-hapten conjugates. No one spacer is beneficial in all assays, but by selection, a hydrophilic spacer is easily identified that confers maximal benefits on the tracer in terms of assay performance. We have disclosed two types (nonionic and polyionic) of spacers that are useful in this regard. It is also evident that from the methodology provided by the current invention, one with ordinary skill in the art could apply the same methodology for the preparation of a variety of tracers using different analytes and different labels. This invention thus discloses tracers of the following generic structures

A—B—C where A is an analyte of interest such as pteroic acid, folic acid, steroids, therapeutic drugs such as theophylline, phenytoin, digoxin, aminoglycosides such as tobramycin phenobarbital etc.; and where B is either (a) polyethylene glycol of molecular weight 150–5000 or (b) is a polyionic spacer derived from spermine or any polyamine where the internal, but not necessarily all, amines have been modified by hydrophilic molecules such as sultones, anhydrides etc.; and where C is a chemiluminescent or fluorescent label.

Preferred acridinium ester conjugates of hydrophilic modifiers include compounds of the following formula:

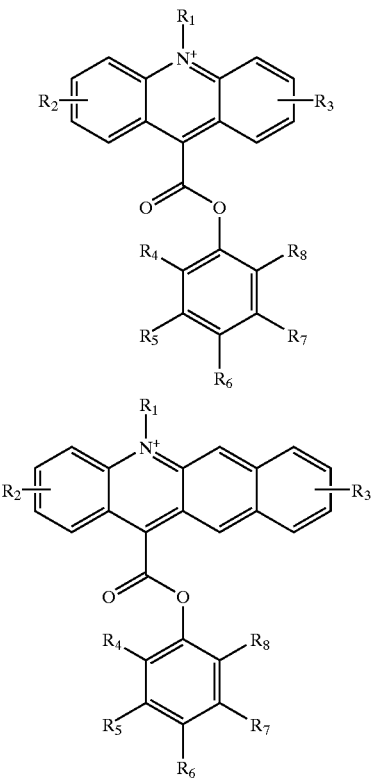

wherein
R$_1$ is alkyl, alkyenyl, alkynyl, aryl, sulfoethyl, sulfopropyl, sulfobutyl, or aralkyl having up to 24 carbons and up to 20 heteroatoms selected from the group consisting of nitrogen, oxygen, phosphorus and sulfur; and R$_2$, R$_3$, R$_5$, R$_7$ are hydrogen, amino, hydroxyl, halide, nitro, —CN, —SO$_3$H, —SCN, —OR, NHCOR, —COR, —COOR, or —CONHR wherein R is alkyl, alkenyl, alkynyl, aryl, aralkyl, having up to 24 carbons and up to 20 heteroatoms selected from the group consisting of nitrogen, oxygen, phosphorus and sulfur; and $R_4$ and $R_8$ are alkyl, alkenyl, alkynyl, aralkyl or alkoxyl having up to 8 carbons with no branching wherein the side chain groups have more than 2 carbons;

$R_6$ represents the following substitutions: $R_6$=R—L—S—$R_{10}$ where R is optionally alkyl, alkenyl, alkynyl, aryl, aralkyl, having up to 24 carbons and up to 20 heteroatoms selected from the group consisting of nitrogen, oxygen, phosphorus and sulfur, L is one of the following linkages: ether, thioether, amide, ester or carbamate;

S is polyethylene glycol from 300 to 5000 molecular weight; or the following structures

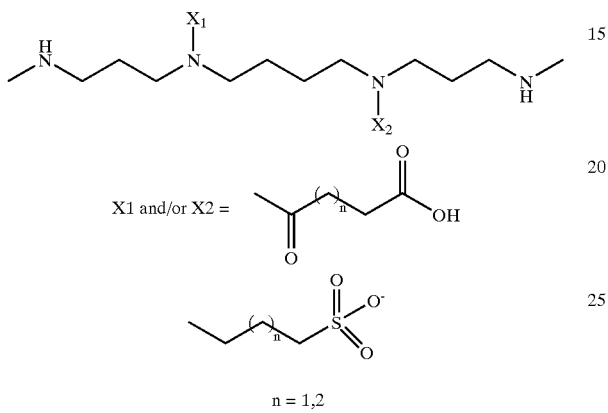

n = 1,2

$R_6$ can be attached, alternatively, at a position of the phenoxy ring, which is meta to the ester linkage (in this case $R_5$ or $R_7$ is attached para to the ester linkage); and $R_{10}$ is an electrophile, a leaving group, or a nucleophile. Preferred embodiments of a pteroate tracer and a folate tracer are illustrated by the following structures.

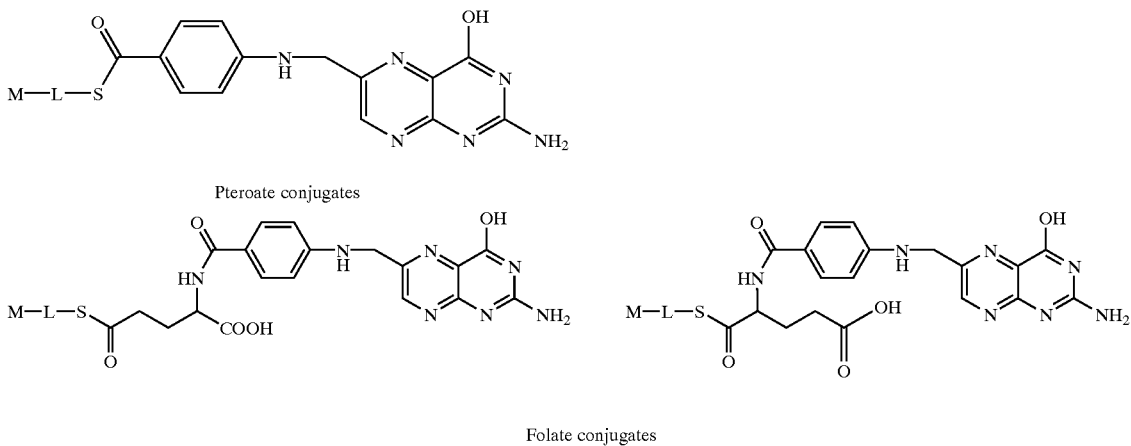

Pteroate conjugates

Folate conjugates where M is an acridinium or benzacridinium ester derivative as defined earlier, except $R_6$ is optionally an alkyl, alkenyl, alkynyl, aryl, aralkyl, having up to 24 carbons and up to 20 heteroatoms selected from the group consisting of nitrogen, oxygen, phosphorus and sulfur; and where L is an amide, ether, thioether, ester or carbamate linkage; and where S is a spacer as defined earlier.

Preferred embodiments of tobramycin and theophylline tracers are illustrated by the following structures.

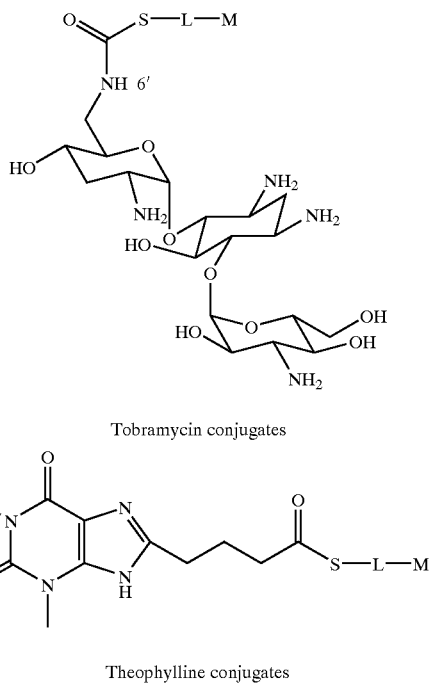

Tobramycin conjugates

Theophylline conjugates where S, L and M are as defined earlier.

The following nonlimiting, representative examples are presented for the purposes of illustration only and are not intened to limit the scope of the patent protection to which the instant invention is entitled and to which protection is defined only by the appended claims.

EXAMPLE 1

The synthesis of NSP-DMAE-HD was accomplished as follows (FIG. 1). 1,6-Diaminohexane (49 mg, 0.42 mmol) in DMF (1 mL) and 0.1 M carbonate pH 9 (1 mL) was treated with NSP-DMAE-NHS (25 mg, 0.042 mmol) in DMF (1 mL). The reaction was stirred at room temperature for 16 hours and was then purified directly by preparative HPLC using a C18 column (20×250 mm) and a 40 min. gradient of 10-->60% MeCN/water each containing 0.05% trifluoroacetic acid (TFA). The product eluted at ~21 minutes. The HPLC fraction containing the product was concentrated under reduced pressure and then lyophilized to dryness to afford a yellow solid. Yield=25 mg (quant.), MALDI-TOF MS 591 obs., (591.73 calc.).

Next, the synthesis of NSP-DMAE-HD-pteroate was accomplished as follows (FIG. 1). Next, $N^{10}$-Trifluoroacetylpteroic acid (2.5 mg, 6.13 umoles) in DMF (400 uL) was treated with ethyl chloroformate (3 uL, 5 equivalents) and diisopropylethyl amine (5.4 uL, 5 equivalents). The reaction was stirred at room temperature for 1 hour. The solvent was then removed under reduced pressure and the residue was treated with NSP-DMAE-HD (1.4 mg, 2.37 umoles) and diisopropylethylamine (2 uL, 11.3 umoles). The resulting reaction was stirred at room temperature for 4 hours and then concentrated. The residue was dissolved in methanol and filtered. The filtrate was purified by HPLC on a C18 column (7.8 mm×25 cm) using a 40 min. gradient of 0-->60% MeCN/water each containing 0.05% TFA; Rt (product)=~27 minutes. The HPLC fraction containing the product was lyophilized to dryness to afford a yellow solid. Yield=0.6 mg (26%); MALDI-TOF MS 983.47 obs. (982.01 calc.).

The above material was stirred in 0.1 M piperidine (500 uL) at room temperature for 4 hours and then the product was purified directly by HPLC as described above; Rt (product)=~26 minutes. The HPLC fraction containing the product was lyophilized to yield a yellow solid. Yield=~0.2 mg, MALDI-TOF MS 889.48 obs., (886 calc.).

EXAMPLE 2

The synthesis of hexaethylene glycol dimethanesulfonate was accomplished as follows. A solution of hexaethyleneglycol (1 g, 3.54 mmol) in chloroform (10 mL) was cooled in an ice-bath under nitrogen and treated with methanesulfonyl chloride (603 uL, 2.2 equivalents) and diisopropylethylamine (1.56 mL, 2.5 equivalents). The reaction was warmed to room temperature and stirred under nitrogen. After 2 hours, additional methanesulfonyl chloride (274 uL, 1.0 equivalent) and disopropylethylamine (749 uL, 1.2 equivalents) was added. After two more hours at room temperature, the reaction was diluted with chloroform and the resulting solution was washed twice with aqueous ammonium chloride followed by brine. The chloroform solution was then dried over magnesium sulfate, filtered and concentrated under reduced pressure. A light yellow oil was obtained. Yield=1.38 g (89%). TLC (10% methanol, 90% chloroform) Rf (product)=0.64; Rf (starting material)=0.42.

Next, the synthesis of diazido hexaethylene glycol was accomplished as follows. A solution of hexaethylene glycol dimethanesulfonate (0.5 g, 1.14 mmol) in DMF (5 mL) was treated with sodium azide (0.31 g, 4.76 mmol). The reaction was heated in an oil-bath at 110° C. under a nitrogen atmosphere for 8 hours. The reaction was then cooled to room temperature and stirred for an additional 16 hours. The DMF was then removed under reduced pressure and the residue was partitioned between chloroform and brine. The chloroform layer was separated, dried over magnesium sulfate, filtered and concentrated under reduced pressure to afford an oil. Yield=0.442 g (quant.); TLC (5% methanol, 95% chloroform) Rf (product)=0.59, Rf (starting material)=0.35.

Figure 2:
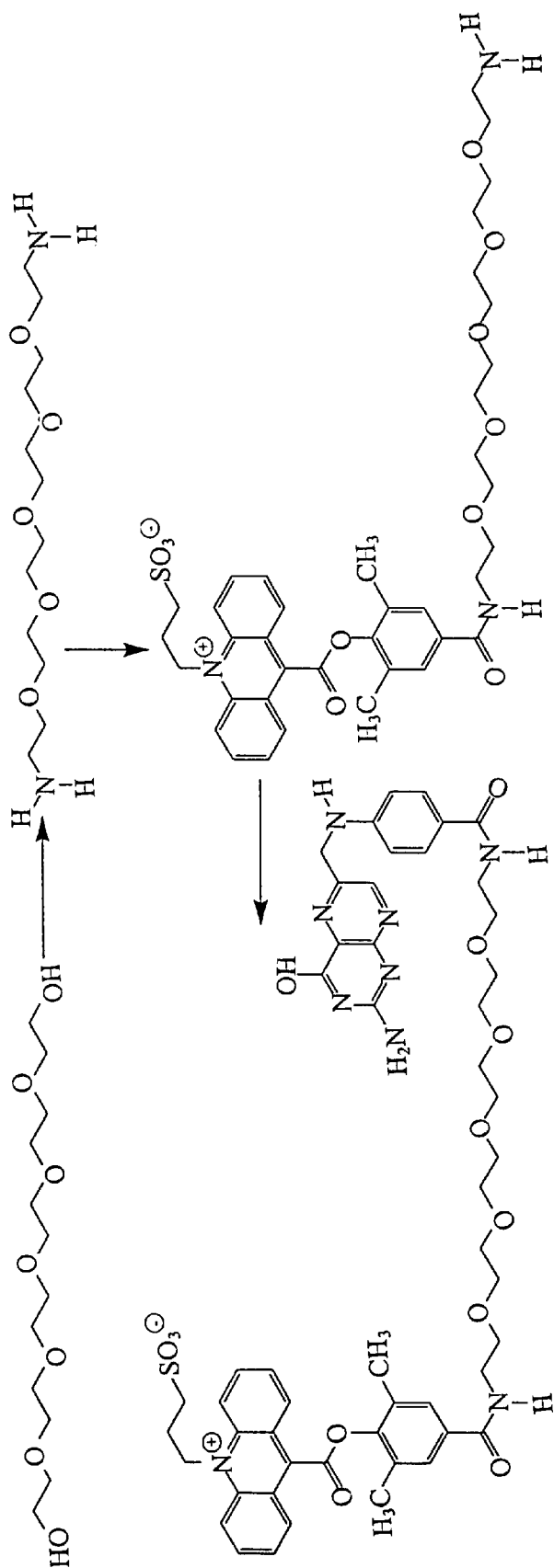
FIG. 2 depicts the synthesis of NSP-DMAE-HEG-pteroate.

Next, the synthesis of diamino hexaethylene glycol (hereinafter referred to as "diaminoHEG") was accomplished as follows (FIG. 2). Next, a solution of diazido hexaethylene glycol (0.44 g 1.32 mmol) in ethyl acetate (15 mL) was treated with 10% Pd on activated carbon (95 mg) and the black reaction mixture was hydrogenated at room temperature. After 16 hours at room temperature, the reaction was filtered and the filtrate was concentrated under reduced pressure to afford an oil. Yield 0.26 g (70%), MALDI-TOF MS 280 obs. 280 calc., TLC (45% methanol, 50% chloroform, 5% ammonium hydroxide) Rf=0.29.

Next, the synthesis of NSP-DMAE-HEG was accomplished as follows (FIG. 2). Next, a solution of diaminoHEG (33 mg, 0.12 mmol) in 2 mL of 1:1, DMF and 0.1 M carbonate pH 9 was treated with NSP-DMAE-NHS (10 mg, 17 umoles). The reaction was stirred at room temperature for 16 hours. The product was purified directly by preparative HPLC on a C18 column (20 mm×300 cm) using a 40 min. gradient of 0-->60% MeCN/water each containing 0.05%; Rt (product)=~21 minutes. The HPLC fraction containing the product was lyophilized to dryness to afford a yellow solid. Yield=10.6 mg (83%), MALDI-TOF MS 757.39 obs., (755.89 calc.).

Next, the synthesis of NSP-DMAE-HEG-pteroate was accomplished as follows (see step (III) of FIG. 2). Next, $N^{10}$-Trifluoroacetyl pteroic acid (5.4 mg, 13.2 umoles) in DMF (0.5 mL) was treated with NHS (7.6 mg, 5 equivalents) and DCC (13.6 mg, 5 equivalents). The reaction was stirred at room temperature under a nitrogen atmosphere. After 2 hours, the reaction was treated with a solution of NSP-DMAE-PEG (3.5 mg, 4.6 umoles) in DMF (400 uL) along with diisopropylethyl amine 2 uL, 11.3 umoles). The resulting solution was stirred at room temperature under a nitrogen atmosphere for 16 hours. The reaction mixture was then purified directly by preparative HPLC on a C18 column (7.8 mm×300 cm) as described earlier; Rt (product)=~24 minutes; MALDI-TOF MS 1148.71.92 obs., (1146.17 calc.).

Next, the above conjugate was stirred in 400 uL of 0.1 M piperidine at room temperature for 1 hour. The reaction was then lyophilized to dryness to afford a yellow solid. HPLC Rt=~21 minutes, MALDI-TOF MS 1051.92 obs., (1050.16 calc.).

EXAMPLE 3

The synthesis of NSP-DMAE-HEG-gamma-folate conjugate was accomplished as follows. N-tert-Butoxycarbonyl-L-glutamic acid alpha-tert-butyl ester (25 mg, 0.082 mmol) was dissolved in MeCN (2 mL) and treated with NHS (14.2 mg, 1.5 equivalents) and DCC (25.5 mg, 1.5 equivalents). The reaction was stirred at room temperature for 1.5 hours. This solution (0.54 mL) was added to a solution of NSP-DMAE-PEG (14 mg, 18.54 umol) in DMF (500 uL) containing diisopropylethylamine (5 ul, 1.5 equivalents). After 2–3 hours additional diisopropylethylamine (2.5 ul) was added along with an additional 540 uL of the active ester solution from above. The resulting reaction was stirred at room temperature for 16 hours. The solvent was then removed under reduced pressure and the residue was dissolved in 2 mL MeCN. This was filtered through glass wool and the filtrate was concentrated under reduced pressure. The crude product was deblocked by stirring in 1 mL of 30% HBr in acetic acid for 2 hours. The product was precipitated with the addition of ether (10 mL). The ether was decanted and the residue was purified directly by HPLC using the same solvent system described earlier, Rt (product)=~20.5 minutes. The HPLC fraction containing the product was lyophilized to dryness to afford 2.8 mg (20%) of the product as a yellow solid. MALDI-TOF MS 888.67 obs. (885.0 calc.).

Next, the synthesis of NSP-DMAE-HEG-gamma-folate was accomplished as follows. $N^{10}$-Trifluoroacetyl pteroic acid (5 mg, 12.25 umoles) in DMF (1 mL) was treated with isobutylchloroformate (4.7 uL, 3 equivalents) and diisopropylethylamine (8 uL, 4 equivalents). The reaction was stirred at room temperature for 1 hour and was then concentrated under reduced pressure. The residue was dissolved in DMF (0.5 mL) and 170 uL of this solution was added to NSP-DMAE-PEG-gamma-glutamate (1.8 mg, 2.03 umoles) along with diisopropylethylamine (1 uL). The reaction was stirred at room temperature for 16 hours and then concentrated under reduced pressure. The residue was dissolved in DMF (1 mL) and purified by HPLC using the same conditions described earlier, Rt (product)=~25.5 minutes. The HPLC fraction containing the product was lyophilized to dryness to afford a yellow solid. MALDI-TOF MS 1276.34 obs., (1275.28 calc.).

Next, the trifluoroacetyl group in the conjugate was removed by stirring in a mixture of 0.1 M piperidine (400 uL) in water and DMF (200 uL) at room temperature. After 6 hours, the product was purified directly by HPLC using the same conditions described earlier, Rt (product)=~22.5 minutes. The HPLC fraction containing the product was lyophilized to give a yellow solid. MALDI-TOF MS 1182.95 obs. (1179.27).

EXAMPLE 4

The synthesis of NSP-DMAE-HEG-alpha-folate conjugate was accomplished as follows. N-tert-Butoxycarbonyl-L-glutamic acid g-tert-butyl ester (20 mg, 0.065 mmol) was dissolved in MeCN (~2 mL) and cooled in ice under a nitrogen atmosphere. N-Hydroxysuccinimide (11.4 mg, 1.5 equivalents) and dicyclohexylcarbodiimide (20.3 mg, 0.0985 mmol) were added and the reaction was warmed to room temperature and stirred for one hour. NSP-DMAE-HEG (14 mg, 0.0185 mmol) in DMF (0.5 mL) was treated with diisopropylethylamine (7 uL, ~2 equivalents) followed by 1.2 mL of the above MeCN solution. The resulting solution was stirred at room temperature under nitrogen for 24 hours. The reaction was then concentrated under reduced pressure. The residue was treated with 2 mL of 30% HBr in acetic acid. After stirring for 3 hours at room temperature, ether was added to precipitate the product which was collected by filtration, rinsed with addtional ether and air dried. The crude product (28 mg) was subjected to preparative HPLC as described earlier. The HPLC fraction containing the product (Rt=~18 min.) was lyophilized to dryness. Yield=4.7 mg (29%). MALDI-TOF MS 910.14 (M+Na+) obs. (885 calc.).

Next, the synthesis of NSP-DMAE-HEG-alpha-folate was accomplished as follows. Next, $N^{10}$-Trifluoroacetylpteroic acid (5 mg, 12.25 umol) in DMF (1 mL) was treated with isobutylchloroformate (4.7 uL, 3 equivalents) and diisopropylethylamine (8 uL, 4 equivalents). The reaction was stirred at romm temperature for 1 hour and then concentrated under reduced pressure. The residue was dissolved in DMF (0.5 mL) and evaporated to dryness again. The compound thus recovered was dissolved in DMF (0.5 mL) and a portion (0.2 mL) of this solution was mixed with NSP-DMAE-HEG-alpha-glutamate (2 mg, 0.0023 mmol). The reaction was stirred at room temperature for 16 hours and then purified directly by preparative HPLC as described earlier (Rt=~26 min.). The HPLC fraction containing the product was lyophilized to dryness to afford a yellow solid. MALDI-TOF MS 1277.47 obs. (1275.28 calc.).

Next, the HPLC purified compound was dissolved in DMF (0.1 mL) and treated with 0.1 M piperidine in water (0.2 mL). The reaction was stirred at room temperature for 3 hours and then purified directly by HPLC as described previously (Rt=~22 min.). The HPLC fraction containing the product was lyophilized to dryness to afford the conjugate. MALDI-TOF MS 1181.42 obs. (1179.27 calc.).

EXAMPLE 5

Several competitive assay parameters were examined for the comparative evaluation of conjugate (tracer) binding functionality. Specifically, these measures included assay precision, assay accuracy, assay sensitivity, fractional non-specific binding, binding affinity and standard curve shape.

Next, arithmetic means for RLUs (Relative Light Units, defined later) resulting from a specific analyte concentration, represented here as $\mu$, were calculated from three replicates. Non-tracer assay reagents also contribute a small though sometimes significant number of RLUs. Hence, a control reaction, containing all assay reagents except tracer, was run in parallel to determine non-tracer reagent background, represented here as n. Mean RLUs, $\mu$, were corrected to represent RLUs obtained from the tracer only, represented here as B, where B=$\mu$–n. Where the analyte concentration was 0.00, the corrected arithmetic mean RLU value was denoted as $B_0$. A non-linear, inverse relationship exists between the analyte concentration present in the standard and the detected RLUs. Consequently, the same antithetical, correlation also relates the analyte concentration to the resultant %B/$B_0$ and can be represented empirically as $$x = 10^{\frac{\log[(y_\infty - y)/(y - y_0)] + b}{-m}}$$

where x is the analyte concentration, and y is the observed signal generated either as %B/$B_0$ or RLUs { [Rodbard, David; Ligand Analysis; (1981); Langon, J.; Clapp, J. (Eds.); Masson Publishing, Inc., N.Y.; pp 45–101], [Nix, Barry; The Immunoassay Handbook; (1994); Wild, David (Ed.); Stockton Press, Inc., New York; pp. 117–123], [Peterman, Jeffrey H.; Immunochemistry of Solid-Phase Immunoassay; (1991); Butler, J. (Ed.); CRC Press, Inc., Boca Raton; pp. 47–65]}.

Four (4) parameters, namely the regression constant, b, the regression coefficient, m, the projected, asymptotic non-specific binding (NSB) at infinite dose (analyte concentration), $y_\infty$, and the asymptotic zero dose response in the absence of analyte, $y_0$, were calculated directly using the iterative, unweighted, four-parameter logistic (4PL) analysis function of the DOSECALC.EXE Rev.1.73 program (Bayer Diagnostics Corp., Walpole, Mass.).

Assay Precision

Precision was was determined from the standard deviation, $sigma_{(n-1)}$, as the percent coefficient of variation, %C.V., where %C.V.=100×$sigma_{(n-1)}/\mu$. Values of less than 10% are desirable (Feldkamp, Carolyn S.; Smith, Stuart W.; Immunoassay: A Practical Guide; (1987); Chan, Daniel W.; Perlstein, Marie T. (Eds.); Academic Press, Inc., San Diego, Calif.; p 49–95).

Assay Accuracy

Accuracy, manifest as percent error (%S) in relation to the 4PL model, was calculated as %S=100×(B−y)/y. Values between ±5% are acceptable (Feldkamp, Carolyn S.; Smith, Stuart W.; Immunoassay: A Practical Guide; (1987); Chan, Daniel W.; Perlstein, Marie T. (Eds.); Academic Press, Inc., San Diego, Calif.; p 49–95).

Assay Sensitivity

The projected minimum detectable analyte concentration, hereby refered to as sensitivity, was determined as the predicted analyte concentration at two standard deviations from the zero dose response.

Fractional Nonspecific Binding

Fractional nonspecific binding (fNSB) in competitive assay is calculated as the quotient of the projected, assymptotic lower limit of y at infinite dose, $y_\infty$, and the total chemiluminescent signal input T. Fractional NSB is a measure of the binding interaction of the conjugate for the solid phase that does not involve the specifically preferred binding associated between the conjugate and the binding protein or antibody on the solid phase. Elevated fNSB is undesirable and may result from one or more of a number of different factors; hydrophobic interaction, exacerbated by the excessive hydrobicity of a conjugate; ionic or polar interactions promoted through the charge density or polarity of the conjugate; and/or a specific but undesirable biological binding interaction. If the assay precision remains unaffected while there is a significant increase in NSB, the apparent slope of the dose response curve will decrease more rapidly as the B0 exceeds the detector's linearity limit.

Conjugate Binding Affinity

Competitive assay $\%B_0/T$ was examined for a comparative evaluation of conjugate binding functionality. Comparison of the resulting quotients is indicative of the relative binding affinity each conjugate has for analyte-binding protein or antibody.

Folate Assay—Assessment of Acridinium Ester-Folate and—Pteroate Conjugate Binding Functionality in a Folate Binding Assay In this assay the acridinium ester-folate conjugates (henceforth referred to as tracers) and folate from folate-containing standards (Bayer Diagnostics Corp., Walpole, Mass.) compete for a limited quantity of bovine folate-binding protein, covalently coupled to a paramagnetic particle solid phase. Folate standards contained folate in concentrations of 0.00, 2.66, 6.52, 12.8, 24.7, 52.7 nM. A reaction mixture, containing 150 μl of folate standard, 50 μl of DTT Reagent and 75 μl of Releasing Agent, was incubated for 2.5 mm. at 37° C. To each reaction 200 μl of solid phase was added and incubated for 2.5 min. at 37° C. Finally 100 μl (280 fmoles) of tracer was added and incubated for 2.5 min. at 37° C. The solid phase was collected on an array of permanent magnets and washed with deionized water to remove unbound tracer. The chemiluminescent reaction was initiated, as described previously. Chemiluminescence data were collected as photons detected by the ACS:180 and expressed in relative light units (RLUs).

Folate Assay Precision

Within run precision was satisfactory for all the folate conjugates, with % C.Vs. being less than 10% over the entire dose response curve. There was no significant difference in overall precision among the conjugates.

TABLE 1

Folate Assay Precision % C.V.

| [Folate] in nM | A1 | A2 | A3 | A4 |
|---|---|---|---|---|
| 0.00 | 1.79 | 1.86 | 0.66 | 0.28 |
| 2.66 | 2.32 | 1.12 | 4.16 | 1.67 |
| 6.51 | 1.03 | 1.69 | 1.11 | 1.56 |

TABLE 1-continued

Folate Assay Precision % C.V.

| [Folate] in nM | A1 | A2 | A3 | A4 |
|---|---|---|---|---|
| 12.8 | 3.41 | 0.95 | 4.30 | 1.94 |
| 24.7 | 1.56 | 2.08 | 4.32 | 2.55 |
| 52.7 | 1.34 | 1.11 | 3.57 | 1.02 |

A1 = NSP-DMAE-HD-pteroate
A2 = NSP-DMAE-HEG-pteroate
A3 = NSP-DMAE-alpha-folate
A4 = NSP-DMAE-gamma-folate Folate Assay Accuracy Accuracy manifest as percent error (%S) with predicted 4PL values was acceptable for all four folate conjugates, being within ±5% over the entire dose response curve. There was no difference in overall accuracy among these conjugates.

TABLE 2

Folate Assay Accuracy % S

| [Folate] in nM | A1 | A2 | A3 | A4 |
|---|---|---|---|---|
| 0.00 | 0.10 | −0.18 | −0.32 | −0.07 |
| 2.66 | −0.46 | 0.59 | 1.31 | 0.26 |
| 6.51 | 0.87 | −0.28 | −2.01 | −0.25 |
| 12.8 | −0.72 | −1.66 | 0.82 | −0.28 |
| 24.7 | 0.16 | 3.61 | 1.72 | 0.82 |
| 52.7 | 0.09 | −2.36 | −1.96 | −0.59 |

A1 = NSP-DMAE-HD-pteroate
A2 = NSP-DMAE-HEG-pteroate
A3 = NSP-DMAE-alpha-folate
A4 = NSP-DMAE-gamma-folate Folate Assay Sensitivity The best folate assay sensitivity was attained with NSP-DMAE-HEG-gamma-folate conjugate. The projected minimum detectable analyte concentration was determined from both the folate concentration at two standard deviations from the 0.00 nM folate dose-response, $B_0-2\text{sigma}_{(n-1)}$. The NSP-DMAE-HEG-gamma-folate conjugate issued the lowest detectable folate concentration, which was followed by the NSP-DMAE-HEG-alpha-folate and NSP-DMAE-HEG-pteroate conjugates in that order. The NSP-DMAE-HD-pteroate tracer was the least sensitive conjugate as a result of the comparatively low $B_0$, curtailed dynamic range and elevated fractional NSB (fNSB). The tracer structural differences may be ranked as follows in accordance with their degree of influence on sensitivity. The folate substitution for pteroate in the tracer structure resulted in an increase in assay sensitivity of at least 2.7-fold when the results of the NSP-DMAE-HEG-alpha-folate tracer were compared with those of the NSP-DMAE-HEG-pteroate tracer. This reflects the relative importance of tracer and analyte structural similarity with regards to folate assay sensitivity. Linking NSP-DMAE-HEG-amine to folate through the glutamate gamma-carboxylate was preferable to conjugation through the alpha-carboxylate, since the gamma-carboxylate union conferred an increase in assay sensitivity of 2.2-fold relative to the alpha-carboxylate isomer. Similarly, the substitution of the hydrophilic HEG-spacer arm for the hydrophobic HD-spacer arm in the pteroate tracer enhanced folate assay sensitivity by 1.4-fold.

TABLE 3

Folate Assay Sensitivity & Binding Data

| | A1 | A2 | A3 | A4 |
|---|---|---|---|---|
| least detectable dose at $B_0$-2 sigma$_{(n-1)}$ in nM | 0.900 | 0.641 | 0.240 | 0.110 |

Relative Light Units

| [folate] in nM | A1 | A2 | A3 | A4 |
|---|---|---|---|---|
| 0.00 | 64,815 | 151,551 | 253,776 | 483,273 |
| 2.66 | 57,652 | 127,445 | 213,252 | 413,729 |
| 6.51 | 47,744 | 102,239 | 173,866 | 336,448 |
| 12.8 | 38,470 | 76,349 | 121,856 | 252,297 |
| 24.7 | 28,321 | 47,877 | 77,193 | 167,239 |
| 52.7 | 19,703 | 28,391 | 42,840 | 94,811 |
| dynamic range | 45,112 | 123,160 | 210,936 | 388,463 |
| fNSB | $8.6 \times 10^{-4}$ | $3.2 \times 10^{-4}$ | $3.9 \times 10^{-4}$ | $3.9 \times 10^{-4}$ |
| % $B_0$/T | 0.53 | 1.15 | 1.50 | 1.88 |

A1 = NSP-DMAE-HD-pteroate
A2 = NSP-DMAE-HEG-pteroate
A3 = NSP-DMAE-alpha-folate
A4 = NSP-DMAE-gamma-folate

NSP-DMAE-FOLATE OR PTEROATE CONJUGATE FRACTIONAL NONSPECIFIC BINDING

Fractional NSB (hereinafter referred to as "fNSB") was significantly reduced with the incorporation of the hydrophilic HEG-spacer into the conjugate structure. The fNSB of the NSP-DMAE-HD-pteroate conjugate was at least 2.2-fold higher than that of the other pteroate or folate based conjugates. The hydrophobic HD spacer increased the nonspecific hydrophobic interaction of the NSP-DMAE-HD-pteroate conjugate with the solid phase. Introduction of the hydrophilic HEG-spacer into the conjugate structure reduced the fNSB as evidenced with the NSPDMAE-HEG-pteroate, NSPDMAE-HEG-alpha-folate and NSPDMAE-HEG-gamma-folate. The slight increase in the fNSB of the latter two folate-based conjugates may reflect a slight increase in the hydrophobicity as introduced with the glutamate moiety.

Conjugate Binding Affinity for Pteroate and Folate-Based Conjugates

The hydrophilic HEG-spacer and the correct orientation of the entire folate moiety are important structural properties for increasing the %$B_0$/T. The %$B_0$/T for NSPDMAE-HEG-gamma-folate conjugate was 3.5-fold higher that that of the NSPDMAE-HD-pteroate conjugate, indicating that both the incorporation of the hydrophilic HEG-spacer and linkage via the gamma-glutamate carboxyl are required for higher binding values. A comparison of the NSPDMAE-HD-pteroate and NSPDMAE-HEG-pteroate binding values indicated that the HEG-spacer conferred 2.2-fold of the overall 3.5-fold increase relative to the HD-spacer. An additional 1.6-fold increase in binding resulted from the incorporation of the gamma-glutamate carboxyl linked folate. A small additional increase of 1.2-fold was noted for the substitution of the alpha-glutamate carboxyl linkage with the gamma-glutamate carboxyl linkage.

Folate Dose Response Curve Shape

The dose response curves of %B/$B_0$ vs. folate concentration indicate that the increased hydrophilicity of the HEG-spacer is important in improving assay sensitivity by increasing the initial slope of the dose response curve. High end dose response is also improved for the same reason, since the high end %B/$B_0$ of the NSPDMAE-HD-pteroate conjugate is at least 10 percentage points higher than the other compared conjugates.

EXAMPLE 6

The synthesis of NSP-DMAE-tobramycin conjugate was accomplished as follows. Tobramycin (1.45 mg, 3.3 umoles) was dissolved in 1:1, DMF/0.1 M carbonate pH 9 (1 mL) and treated with a solution of NSP-DMAE-NHS ester (2 mg, 3.3 umoles) in DMF (0.2 mL) added periodically at five minute intervals. The reaction was stirred at room temperature for 2 hours and then at 4° C. for an additional 24–36 hours. The product was purified by preparative HPLC using a C18 column (7.8 mm×30 cm) and a 40 min. gradient of 10-->60% MeCN/0.1 M TEAA pH 5 at a flow rate of 2.3 mL/min. and UV-detection at 260 nm. The conjugate eluted at 17–18 minutes. The HPLC fraction containing the conjugate was lyophilized to dryness to afford a white, amorphous solid. ES MS 943.7 obs. (943 calc.).

EXAMPLE 7

The synthesis of NSP-DMAE-HEG glutarate NHS ester was accomplished as follows. NSP-DMAE-HEG (20 mg, 23 umoles) in DMF (1–2 mL) was treated glutaric anhydride (4.2 mg, 1.5 equivalents) and diisopropylethylamine (12 uL, 3 equivalents). The reaction was stirred at room temperature. After 6 hours additional glutaric anhydride (3.2 mg) was added and the reaction was continued overnight. The product was purified by preparative HPLC on a C18 column (20×250 mm) and a 40 min. gradient of 10-->60% MeCN/water each containing 0.05% TFA at a flow rate of 16 mL/min and UV detection at 260 nm. The HPLC fraction containing the product (Rt=~20–21 min.) was lyophilized to dryness to yield a yellow solid. Yield=7.3 mg (32%). MALDI-TOF MS 873.5 obs. (870 calc.).

This compound (7.3 mg, 8.4 umoles) in DMF (1 mL) was treated with N-hydroxysuccinimide (4.8 mg, 5 eq.) and dicyclohexylcarbodiimide (8.7 mg, 5 eq.). The reaction was stirred at room temperature under nitrogen. After ~16 hours, the reaction was filtered through glass wool and the product was isolated by HPLC as described above (Rt=~23–24 min.). The HPLC fraction containing the product was lyophilized to dryness to give a yellow solid. Yield=2.3 mg (28%). MALDI-TOF MS 970.82 obs. (967.1 calc.). Next, the synthesis of NSP-DMAE-HEG-glutarate-tobramycin conjugate was accomplished as follows. Tobramycin (1 mg, 2.14 umoles) in 0.1 M carbonate pH 8.5 (0.3 mL) was treated with NSP-DMAE-HEG-glutarate-NHS ester (0.5 mg, 0.52 umol) in DMF (0.15 mL), added in 25 uL aliquots every minute. The reaction was stirred at room temperature for 16 hours and then purified directly by HPLC (Rt=~18 min.) as described previously for the NSP-DMAE-tobramycin conjugate. Yield=~0.1 mg. MALDI-TOF MS 1323.38 obs. (1320.49 calc.).

EXAMPLE 8

Tobramycin Assay—Assessment of Acridinium Ester—Tobramycin Conjugate Binding Functionality in a Tobramycin Binding Assay In this assay the acridinium ester-tobramycin conjugates (henceforth referred to as tracers) and tobramycin from tobramycin—containing standards (Bayer Diagnostics, Walpole, Mass.) compete for a limited amount of murine IgG, monoclonal antibody covalently coupled to a paramagnetic solid phase. Tobramycin standards contained tobramycin at concentrations of 0.00, 1.07, 2.14, 4.28, 8.56, 17.1, 25.7 and 34.2 µM. The reaction is initiated by mixing 50 µl tobramycin standard, 400 µl of solid phase and 100 µl of tracer. The reaction mixture was incubated for 7.5 minutes at 37° C. The solid phase was collected on an array of permanent magnets and washed with deionized water to remove any unbound tracer. The chemiluminescent reaction was initiated, as described previously. Data were collected as photons detected by the ACS:180 and expressed as RLU. A non-linear, inverse relationship exists between the tobramycin concentration present in the standard and the RLUs detected by the ACS:180. The acquired data was processed as previously described for the folate assay data treatment.

Tobramycin Assay Precision

Within run precision was excellent for both tobramycin tracers, with % C.Vs. being well below 10% over the entire standard curve. There was no difference in overall precision between the two conjugates.

TABLE 4

Tobramycin Assay Precision % C.V.

| [tobramycin] in microM | A1 | A2 |
|---|---|---|
| 0.00 | 0.39 | 0.45 |
| 1.07 | 0.71 | 1.17 |
| 2.14 | 1.81 | 2.34 |
| 4.28 | 1.67 | 0.79 |
| 8.56 | 2.98 | 3.18 |
| 17.1 | 1.31 | 2.51 |
| 25.7 | 2.19 | 3.26 |
| 34.2 | 1.60 | 2.93 |

A1 = NSP-DMAE-tobramycin conjugate
A2 = NSP-DMAE-HEG-glutarate-tobramycin conjugate Tobramycin Assay Accuracy Accuracy evinced as percent error with predicted 4PL values was acceptable for both tobramycin tracers, being for the most part within ±5% over the entire standard curve. There was no difference in overall accuracy for these conjugates.

TABLE 5

Tobramycin Assay Accuracy % S

| [tobramycin] in microM | A1 | A2 |
|---|---|---|
| 0.00 | 0.01 | 0.00 |
| 1.07 | -0.11 | -0.43 |
| 2.14 | 0.05 | 1.91 |
| 4.28 | 1.21 | -1.89 |
| 8.56 | -2.69 | -2.61 |
| 17.1 | -0.74 | -0.74 |
| 25.7 | 0.80 | 2.54 |
| 34.2 | 2.90 | 5.54 |

A1 = NSP-DMAE-tobramycin conjugate
A2 = NSP-DMAE-HEG-glutarate-tobramycin conjugate Tobramycin Assay Sensitivity The best tobramycin assay sensitivity was achieved using the NSP-DMAE-HEG-glut-tobramycin conjugate. The predicted sensitivity from assay results using the NSP-DMAE-HEG-glut-tobramycin conjugate was 1.7-fold lower than that using NSP-DMAE-tobramycin conjugate. We conclude therefore, that the hydrophilic HEG-glut-spacer must be integrated into the tobramycin conjugate structure in order to attain improved tobramycin assay sensitivity. The increase in sensitivity resulted from the steeper incline of the slope when the HEG-glut-spacer was incorporated into the conjugate.

TABLE 6

Tobramycin Assay Sensitivity & Binding Data

| | A1 | A2 |
|---|---|---|
| least detectable dose at $B_0$-2sigma$_{(2-1)}$ in microM | 10.19 | 5.98 |

| [tobramycin] in microM | Relative Lights Units | |
|---|---|---|
| 0.00 | 1,442,713 | 1,152,351 |
| 1.070 | 738,611 | 408,291 |
| 2.14 | 495,195 | 248,234 |
| 4.28 | 302,218 | 140,911 |
| 8.56 | 175,943 | 78,004 |
| 17.1 | 103,452 | 44,041 |
| 25.7 | 77,712 | 32,297 |
| 34.2 | 64,766 | 26,443 |
| dynamic range | 1,377,947 | 1,125,908 |
| fNSB | $1.15 \times 10^{-2}$ | $4.31 \times 10^{-3}$ |
| % $B_0$/T | 65.1 | 56.6 |

A1 = NSP-DMAE-tobramycin conjugate
A2 = NSP-DMAE-HEG-glutarate-tobramycin conjugate NSP-DMAE-Tobramycin Conjugate Fractional Nonspecific Binding Fractional NSB was significantly reduced with the incorporation of the hydrophilic HEG-glut-spacer into the conjugate structure. Fractional NSB of the NSP-DMAE-HEG-glut-tobramycin conjugate was 2.7-fold lower than that of the NSP-DMAE-tobramycin conjugate.

Conjugate Binding Affinity for Tobramycin-Based Conjugates

Incorporation of the hydrophilic HEG-glut-spacer lowered the %$B_0$/T of the tobramycin conjugate by 8.9 percentage points.

Tobramycin Dose Response Curve Shape

The dose response curves of %B/$B_0$ vs. tobramycin concentration indicate that the increased hydrophilicity of the HEG-glut-spacer steepened the initial slope of the dose response curve, thereby increasing assay sensitivity.

EXAMPLE 9

The synthesis of NSP-DMAE-HD-theophylline conjugate was accomplished as follows. 8-Carboxypropyltheophylline (10 mg, 0.038 mmol) in DMF (3 mL) was treated with N-hydroxysuccinimide (21.6 mg, 0.188 mmol) and dicyclohexylcarbodiimide (38.8 mg, 0.188 mmol). The resulting solution was stirred at room temperature for 16 hours. HPLC analysis on a C18 column (4.6 mm×300 mm) using a gradient of 10-->60% MeCN/water (each containing 0.05% TFA) over 40 minutes at a flow of 1 mL/min. and UV-detection at 260 nm showed ~50% conversion; Rt (starting material)=10 min., Rt (product)=14 min. This material was used as such without purification for subsequent coupling reactions. Next, NSP-DMAE-HD (3.3 mg, 0.00564 mmol) in methanol (0.2 mL) was treated with disopropylethylamine (2.95 uL, 0.0169 mmol) and 0.9 mL of the above DMF solution of 8-carboxypropyltheophylline NHS ester (1.5 mg, 1 eq.). The reaction was stirred at room temperature for 16 hours and was then purified by HPLC on a C18 column (20×300 mm) using a 40 min. gradient of 10-->60% MeCN/water (each containing 0.05% TFA) at a flow rate of 16 mL/min. and UV detection at 260 nm. Rt (conjugate)=~23 min. The HPLC fraction containing the product was lyophilized to dryness to afford a yellow solid. Yield=4.3 mg (91%); MALDI-TOF MS 840.39 obs. (839.97 calc.).

EXAMPLE 10

The synthesis of NSP-DMAE-SPDS-theophylline conjugate was accomplished as follows. NSP-DMAE-HEG (6.5 mg, 0.0086 mmol) was dissolved in methanol (0.2 mL) and treated with diisopropylethylamine (3.93 uL, 3 eq.) followed by the NHS ester of carboxytheophylline (2 mg, 1 eq.) in DMF (1.2 mL). The resulting reaction was stirred at room temperature for 16 hours. The reaction was then filtered through glass wool and purified directly by HPLC as described previously (Rt=22 min.). The HPLC fraction containing the product was lyophilized to dryness to afford a yellow solid. Yield=3.6 mg (42%); MALDI-TOF MS 1004.36 obs. (1002.11 calc.).

EXAMPLE 11

The synthesis of bis(phthalimido)spermine was accomplished as follows. Spermine (275 mg, 0.00138 mol) in chloroform (5 mL) was treated with N-carbethoxyphthalimide (0.608 g, 0.00278 mol). The reaction was stirred at romm temperature for 40 minutes by which time TLC analysis (5% ammonium hydroxide, 95% methanol) showed complete conversion (Rf=0.42). The reaction mixture was then evaporated to dryness and the crude material was used a such for the next reaction. MALDI-TOF MS 463.8 obs. (462.55 calc.) Next, the synthesis of bis(phthalimido)spermine disulfonate was accomplished. Bis(phthalimido)spermine (0.4 g) was mixed with 1,3-propane sultone (4 g) in a sealed tube and the mixture was heated in an oil-bath at 140° C. for 16 hours. The reaction mixture was then cooled to room temperature and the residue was partitioned between water and ethyl acetate. The cloudy aqueous layer was separated and extracted twice with ethyl acetate. The ethyl acetate extracts were discarded. The aqueous layer was concentrated under reduced pressure to afford a sticky solid. Yield=0.53 g (87%). MALDI-TOF MS 708.61 obs. (706.84 calc.).

Next, the synthesis of spermine disulfonate (SPDS) was accomplished as follows. Bis(phthalimido)spermine disulfonate (0.53 g) was dissolved in methanol (15–20 mL) and treated with hydrazine (0.5 mL). The resulting solution was stirred at room temperature for 24 hours and then concentrated under reduced pressure. The residue was dissolved in ~5 mL of 20% ammonium hydroxide, 80% methanol and evaporated to dryness. This process was repeated once. Finally, the residue was dissolved in a mixture of methanol (1 mL), water (1.5 mL) and triethylamine (1.5 mL) and the solution was evaporated to dryness again. The crude product obtained after this was purified by preparative TLC on silica gel using 10% ammonium hydroxide 90% methanol as eluent. The compound was extracted from the TLC plates using 25–30% ammonium hydroxide in methanol and evaporated to dryness. The residue was evaporated to dryness once more from a solution of methanol (5), water (5) and triethylamine (1). This process was repeated twice. In the end, a white solid was obtained. Yield=0.2 g (57%). MALDI-TOF MS 470.36 (M+Na+) obs. (446.63).

Next, the synthesis of NSP-DMAE-SPDS was accomplished as follows. Spermine disulfonate (25 mg, 0.056 mmol) was dissolved in 2.0 mL of water/0.2 M sodium bicarbonate pH 8.5 (1:4) and treated with NSP-DMAE-NHS (4.7 mg, ⅐ eq.) followed by 0.5 mL DMF. The reaction was stirred at room temperature for 16 hours. HPLC analysis using a C18 column (3.9×300 mm) and a 40 min. gradient of 10-->60% MeCN/water (each containing 0.05% TFA) at a flow rate of 1 mL/min. and UV detection at 260 nm showed product at Rt=14.5 min. This was isolated by preparative HPLC using a 25×300 mm column and the same gradient. The HPLC fraction containing the product was lyophilized to dryness to afford a yellow solid. Yield=2.4 mg (33%). MALDI-TOF MS 926.9 obs. (924.17 calc.).

Next, the synthesis of NSP-DMAE-SPDS-theophylline conjugate was accomplished as follows. NSP-DMAE-SPDS (5.2 mg, 0.00564 mmol) was dissolved in a mxiture of DMF (0.16 mL) and 0.1 M phosphate pH 8 (40 uL) and treated with a solution of 8-carboxypropyltheophylline NHS ester (1.5 mg, 1 eq.) in DMF (0.9 mL). The reaction was stirred at room temperature for for 16 hours. The conjugate was isolated by preparative HPLC on a C18 column as described above; Rt(conjugate) 15 min. The HPLC fraction containing the product was lyophilized to dryness. Yield=5.6 mg (85%); MALDI-TOF MS 1171.89 obs. (1172.41 calc.).

EXAMPLE 12

The synthesis of spermine dicarboxylate was accomplished as follows. Spermine (296 mg, 0.00146 mol) in chloroform (10 mL) was treated with N-carbethoxyphthalimide (658 mg, 2.05 eq.). The reaction was stirred at room temperature under nitrogen. After 1.5 hours, succinic anhydride (0.440 g, 2 eq.) was added along with pyridine (353 uL, 3 eq.) and diisopropylethylamine (774 uL, 3 eq.). The reaction was stirred at room temperature for 16 hours. TLC analysis (90% chloroform, 9% methanol, 1% acetic acid) showed clean conversion to a major product (Rf=0.43). The reaction mixture was then treated with hydrazine (0.45 mL, ~10 eq.) and methanol (10 mL). The reaction was stirred at room temperature. After 1–2 hours, a crystalline precipitate appeared in the reaction mixture. After 3–4 hours, total reaction time, the reaction was concentrated under reduced pressure. The residue was suspended in acetone and filtered. The precipitate was rinsed with acetone and dissolved in water (50 mL) with triethyl amine (1.5 mL). This was concentrated under reduced pressure to afford a white powder. MALDI-TOF MS 403.7 obs. (402.49).

Next, the synthesis of NSP-DMAE-SPDC was accomplished as follows. Spermine dicarboxylate (45 mg, 0.112 mmol) was dissolved in 2 mL of 0.1 M carbonate pH 9 (adjusted with 5N NaOH) and treated with a solution of NSP-DMAE-NHS ester (10.5 mg, 0.0178 mmol) in DMF (2 mL). The reaction was stirred at room temperature for 16 hours. The product was isolated by preparative HPLC on a C18 column (20×300 mm) using a 40 min. gradient of 0-->40% MeCN/water (each containing 0.05% TFA) at a flow rate of 16 mL/min. and UV detection at 260 nm; Rt (product)=18 min. The HPLC fraction containing the product was lyophilized to dryness to afford a yellow solid. Yield=6.7 mg (43%); MALDI-TOF MS 877.53 obs. (878.01 calc.).

Next, the synthesis of NSP-DMAE-SPDC-theophylline conjugate was accomplished as follows. NSP-DMAE-SPDC (1 mg, 0.00114 mmol) was dissolved in 0.1 mL DMF and 8-carboxypropyltheophylline (1 mg, 0.00262 mmol) was added along with diisopropylethylamine (2 uL, 2 eq.). The reaction was stirred at room temperature for 16 hours and was then purified directly by HPLC on a C18 column (20×300 mm) using a gradient of 10-->60% MeCN/water (each containing 0.05% TFA) over 40 min. at a flow rate of 16 mL/min. and UV detection at 260 nm; Rt (conjugate)=18 min. The HPLC fraction containing the product was lyophilized to dryness. Yield=1.9 mg (quant.); MALDI-TOF MS 1127.24 obs. (1126.25 calc.)

EXAMPLE 13

In this assay the acridinium ester-theophylline conjugates (henceforth referred to as tracers) and theophylline from theophylline-containing standards (Bayer Diagnostics, Walpole, Mass.) compete for a limited amount murine IgG, monoclonal anti-theophylline antibody which was covalently coupled to a paramagnetic particle solid phase. A reaction mixture containing 20 microL of theophylline standard, 450 microL of solid phase and 100 microL (59 fmoles) of tracer was incubated at 37° C. for 7.5 min. Theophylline standards contained theophylline in concentrations of 0.00, 6.94, 13.9, 27.7, 55.5, 111 and 222 $\mu$M. The solid phase was collected on an array of permanent magnets and washed twice with deionized water to remove unbound tracer. The chemiluminescent reaction was initiated, as described previously. Data were collected as photons detected by the ACS:180 and expressed as RLU. A non-linear, inverse relationship exists between the theophylline concentration present in the standard and the RLUs detected by the ACS:180. The acquired data was processed as previously described for the folate assay data treatment.

Theophylline Assay Precision

Within run precision was satisfactory for all the theophylline tracers, with % C.Vs. being less than 10% over the entire standard curve.

TABLE 7

Theophylline Assay Precision % C.V.

| [theophylline] in microM | A1 | A2 | A3 | A4 |
|---|---|---|---|---|
| 0.00 | 0.67 | 1.83 | 1.70 | 0.79 |
| 6.94 | 2.57 | 2.00 | 2.94 | 2.52 |
| 13.9 | 1.86 | 5.00 | 1.64 | 0.33 |
| 27.8 | 1.19 | 0.36 | 2.13 | 5.82 |
| 55.5 | 5.81 | 2.01 | 2.33 | 3.51 |
| 111 | 0.97 | 2.04 | 1.59 | 1.59 |
| 222 | 2.94 | 1.37 | 4.34 | 7.44 |

A1 = NSP-DMAE-HD-theophylline
A2 = NSP-DMAE-PEG-theophylline
A3 = NSP-DMAE-SPDS-theophylline
A4 = NSP-DMAE-SPDC-theophylline Theophylline Assay Accuracy Accuracy specified as percent error with predicted 4PL values was satisfactory for all of the theophylline conjugates, being well within ±5% over the entire standard curve. There was no difference in overall accuracy among these conjugates.

TABLE 8

Theophylline Assay Accuracy % Error

| [theophylline] in microM | A1 | A2 | A3 | A4 |
|---|---|---|---|---|
| 0.00 | −0.04 | 0.00 | 0.01 | −0.01 |
| 6.94 | 0.49 | 0.09 | −0.26 | 0.22 |
| 13.9 | −1.20 | −0.43 | 1.10 | −0.58 |
| 27.8 | 1.18 | 0.79 | −2.07 | −0.08 |

TABLE 8-continued

Theophylline Assay Accuracy % Error

| [theophylline] in microM | A1 | A2 | A3 | A4 |
|---|---|---|---|---|
| 55.5 | 0.17 | −0.02 | 1.74 | 2.08 |
| 111 | −1.21 | −2.26 | 0.73 | −0.95 |
| 222 | 0.54 | 2.52 | −1.51 | −1.71 |

A1 = NSP-DMAE-HD-theophylline
A2 = NSP-DMAE-PEG-theophylline
A3 = NSP-DMAE-SPDS-theophylline
A4 = NSP-DMAE-SPDC-theophylline Theophylline Assay Sensitivity The best theophylline assay sensitivity was effected using the NSP-DMAE-SPDC-theophylline conjugate. NSP-DMAE-HEG-theophylline and NSP-DMAE-SPDS-theophylline gave minimal detectable doses that were higher than that of the NSP-DMAE-HD-theophylline. The decreased sensitivity in the case of NSP-DMAE-HEG-theophylline and NSP-DMAE-SPDS-theophylline may result from slightly elevated imprecision for the zero dose.

TABLE 9

Theophylline Assay Sensitivity & Binding Date

| | A1 | A2 | A3 | A4 |
|---|---|---|---|---|
| least detectable dose at $B_0$-2 sigma$_{(n-1)}$ in microM | 0.272 | 0.497 | 0.311 | 0.089 |

| [theophylline] in microM | Relative Light Units | | | |
|---|---|---|---|---|
| 0.0 | 715,394 | 539,268 | 769,617 | 648,559 |
| 6.94 | 511,553 | 351,686 | 442,911 | 317,389 |
| 13.0 | 392,914 | 261,193 | 313,980 | 214,678 |
| 27.7 | 268,471 | 173,922 | 201,019 | 133,152 |
| 55.5 | 165,325 | 105,453 | 118,487 | 77,581 |
| 111 | 96,836 | 60,938 | 66,996 | 44,253 |
| 222 | 57,387 | 35,158 | 37,668 | 25586 |
| dynamic range | 658,007 | 504,110 | 731,949 | 622,973 |
| fNSB | 1.27 × $10^{-2}$ | 6.40 × $10^{-3}$ | 3.47 × $10^{-3}$ | 4.04 × $10^{-3}$ |
| % $B_0$/T | 56.8 | 52.0 | 54.7 | 56.9 |

A1 = NSP-DMAE-HD-theophylline
A2 = NSP-DMAE-PEG-theophylline
A3 = NSP-DMAE-SPDS-theophylline
A4 = NSP-DMAE-SPDC-theophylline NSP-DMAE-Theophylline Conjugate Fractional Nonspecific Binding Fractional NSB was significantly reduced with the incorporation of the hydrophilic spacers into the conjugate structures. The fNSB of the NSP-DMAE-SPDS-theophylline was the lowest overall being 3.7-fold lower than that of the NSP-DMAE-HD-theophylline conjugate. The NSP-DMAE-SPDC-theophylline and NSP-DMAE-HEG-theophylline conjugates had fNSBs that were 3.1- and 2.0-fold lower, respectively. The more highly polar or charged spacers confer lower fNSBs upon their respective conjugates.

Conjugate Binding Affinity For Theophylline-Based Conjugates

No appreciable difference could be seen in the %$B_0$/Ts of the various conjugates.

Theophylline Dose Response Curve Shape

The dose response curves of %B/$B_0$ vs. theophylline concentration indicate that the increased hydrophilicity of the spacer increases the initial slope of the dose response curve, thereby increasing sensitivity of the assay assuming an equivalence in precision. The NSP-DMAE-SPDC-theophylline conjugate elicited the steepest decline in the initial slope followed by $1^{st}$ NSP-DMAE-SPDS-theophylline; $2^{nd}$ NSP-DMAE-HEG-theophylline; & $3^{rd}$ NSP-DMAE-HD-theophylline (in that order).

We claim:

1. A conjugate with improved hydrophilicity having the general structure A—B—C, wherein, A is an analyte;

B is a hydrophilic modifier selected from the group consisting of polyethylene glycol having a molecular weight of about 280–5000, or a polyionic spacer derived from a polyamine where the internal, but not necessarily all the amines have been modified by hydrophilic molecules; and C is a chemiluminescent acridinium compound containing a phenyl moiety with an ester linkage wherein the hydrophilic modifier is conjugated meta or para to the ester linkage.

2. The conjugate of claim 1, wherein the analyte is a macromolecule selected from the group consisting of antibodies, antibody fragments, avidin, streptavidin, neutravidin, nucleic acids, receptors, binding protein, allergens, cells, viruses and synthetic polymers.

3. The conjugate of claim 1, wherein the analyte is a small molecule selected from the group consisting of therapeutic drugs, steroids, hormones, vitamins and small peptides.

4. The conjugate of claim 1, wherein the hydrophilic modifier is selected from the group consisting of hexaethylene glycol and spermine derivatives.

5. Acridinium ester conjugates of hydrophilic modifiers with the following structure:

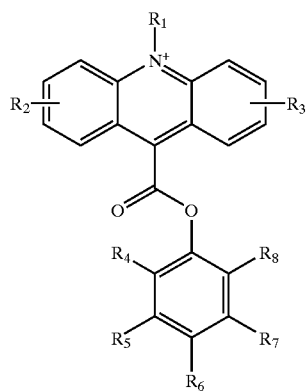

wherein, $R_1$ is alkyl, alkyenyl, alkynyl, aryl, sulfoethyl, sulfopropyl, sulfobutyl, or aralkyl having up to 24 carbons and up to 20 heteroatoms selected from the group consisting of nitrogen, oxygen, phosphorus and sulfur;

$R_2$, $R_3$, $R_5$, $R_7$ are hydrogen, amino, hydroxyl, halide, nitro, —CN, $SO_3H$, —SCN, —OR, NHCOR, —COR, —COOR, or —CONHR, wherein R is alkyl, alkenyl, alkynyl, aryl, aralkyl, having up to 24 carbons and up to 20 heteroatoms selected from the group consisting of nitrogen, oxygen, phosphorus and sulfur;

$R_4$ and $R_8$ are alkyl, alkenyl, alkynyl, aralkyl or alkoxyl having up to 8 carbons;

$R_6$=R—L—S—$R_{10}$, wherein $R_6$ has greater than 5 heteroatoms and is alternatively attached on a position of the phenoxy ring which is meta to the ester linkage such that $R_5$ or $R_7$ is attached para to the ester linkage;

R is optionally alkyl, alkenyl, alkynyl, aryl, aralkyl, having up to 24 carbons and up to 20 heteroatoms selected from the group consisting of nitrogen, oxygen, phosphorus and sulfur;

L is selected from the group consisting of ether, thioether, amide, ester and carbamate;

S is selected from the group consisting of polyethylene glycol varying from 280 to 5000 molecular weight and the following structures:

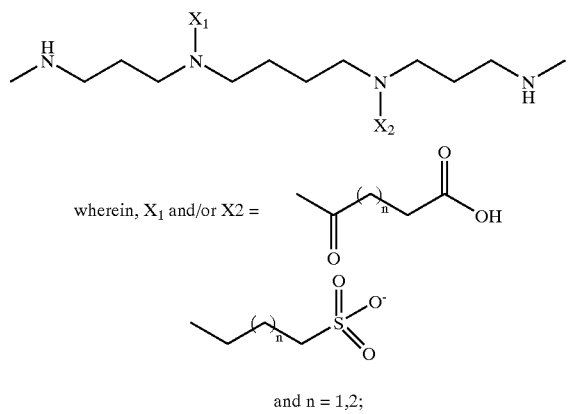

and $R_{10}$ is an electrophile, a leaving group, or a nucleophile.

6. The acridinium ester conjugate of claim 5, with the following structure:

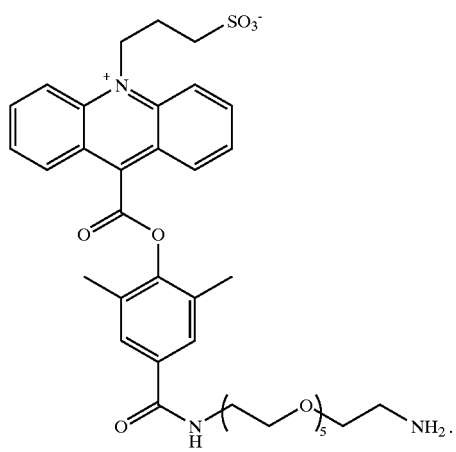

7. The acridinium ester conjugate of claim 5, with the following structure:

8. The acridinium ester conjugate of claim 5, with the following structure:

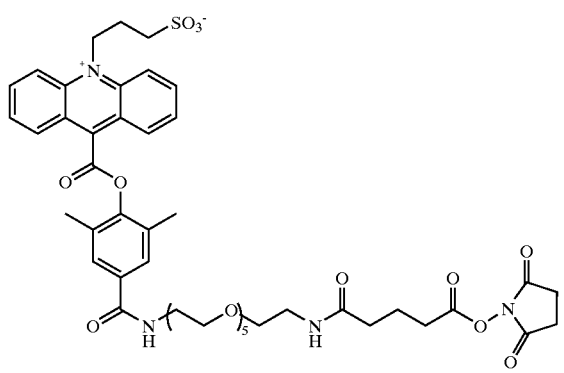

9. The acridinium ester conjugate of claim 5, with the following structure:

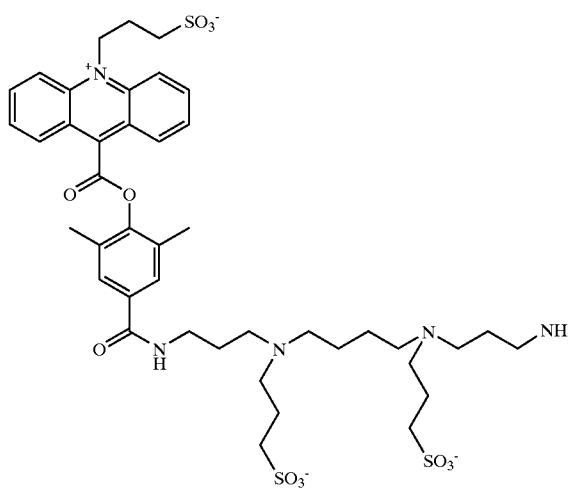

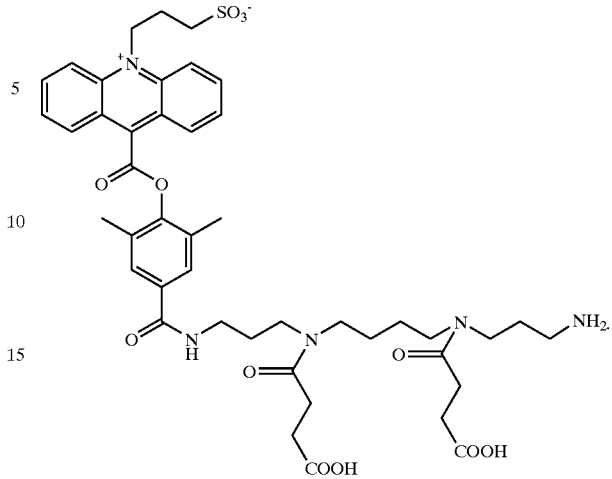

10. A further acridinium ester conjugate comprising the acridinium ester conjugate of claim 5 and an analyte.

11. The further acridinium ester conjugate of claim 10, wherein the analyte is a small molecule selected from the group consisting of therapeutic drugs, steroids, hormones, vitamins and small peptides.

12. The further acridinium conjugate of claim 10, wherein the analyte is a macromolecule selected from the group consisting of antibodies, antibody fragments, avidin, streptavidin, neutravidin, nucleic acids, receptors, binding protein, allergens, cells, viruses and synthetic polymers.

13. The further acridinium ester conjugate of claim 11 wherein said small molecule is pteroic acid and said conjugate has the following structure:

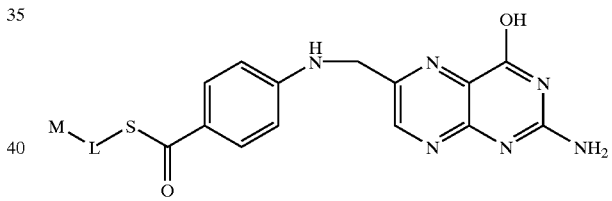

wherein M is the acridinium ester.

14. The further acridinium ester conjugate of claim 13, having the following structure:

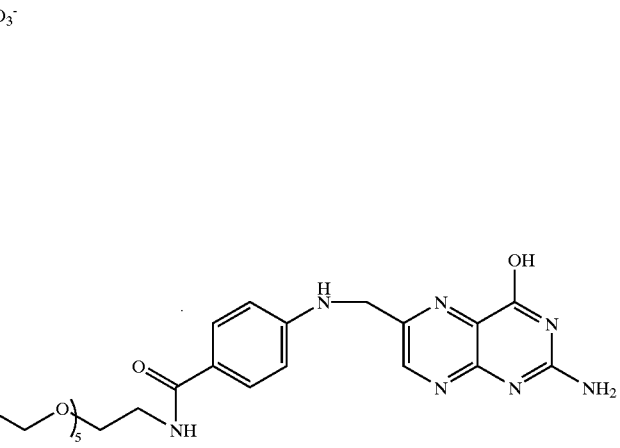

15. The further acridinium ester conjugate of claim 13, having the following structure:
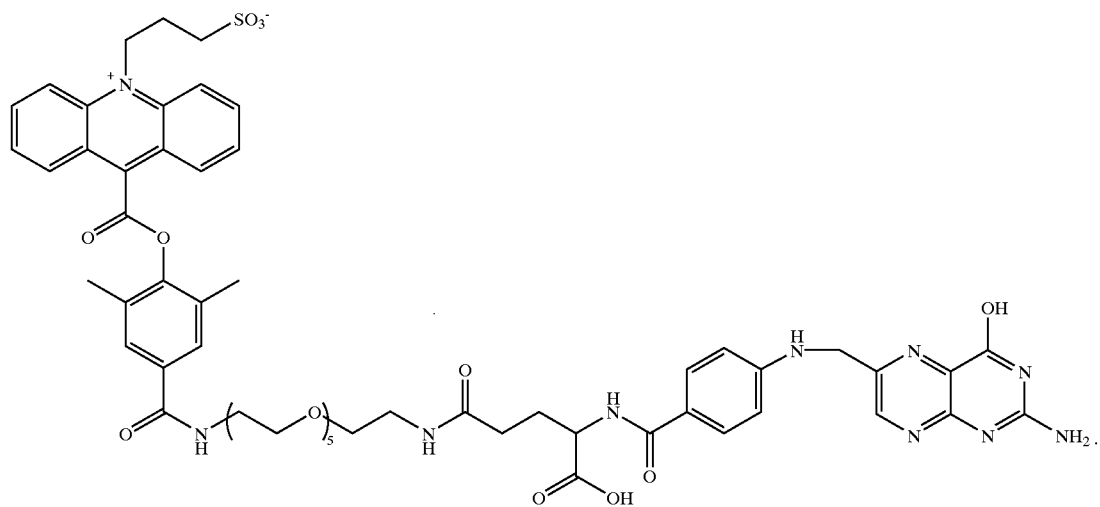
16. The further acridinium ester conjugate of claim 13, having the following structure:
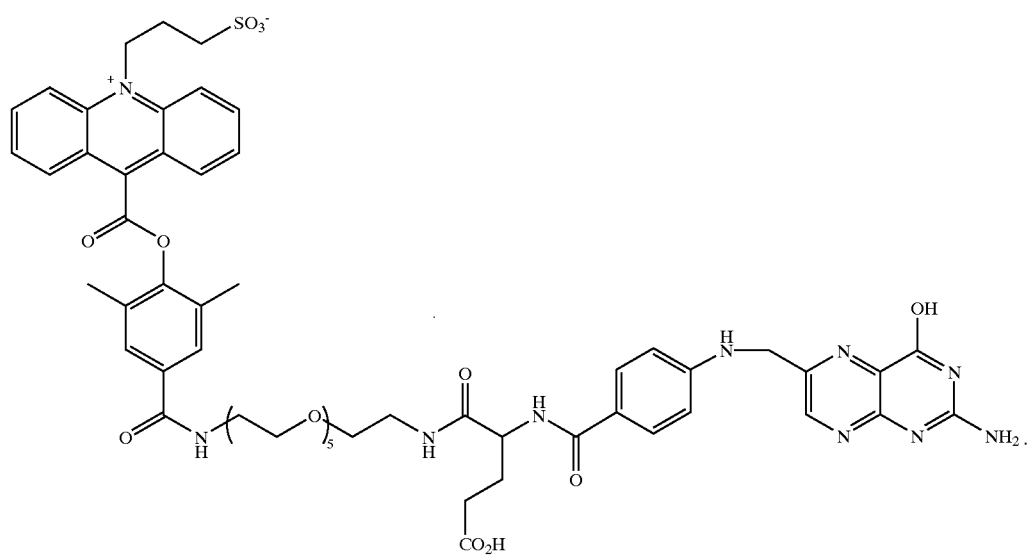
17. The further acridinium ester conjugate of claim 11, wherein said therapeutic drug is tobramycin and said conjugate has the following structure:

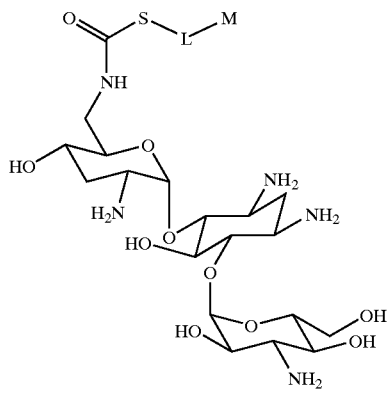

wherein M is the acridinium ester.

18. The further acridinium ester conjugate of claim 17 having the following structure:

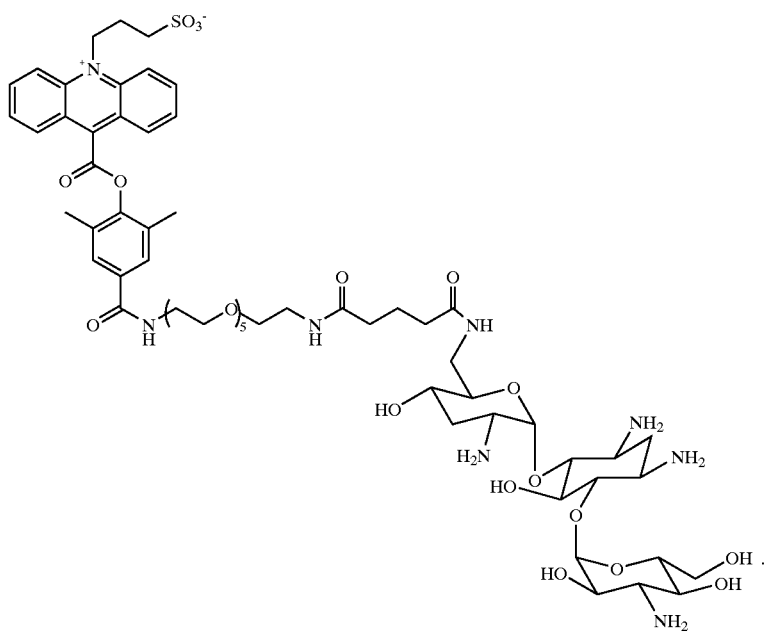

19. The further acridinium ester of claim 11, where said therapeutic drug is theophylline and said conjugate has the following structure:

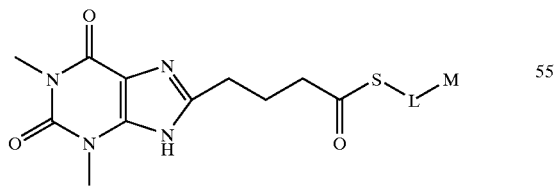

wherein M is the acridinium ester.

20. The further acridinium ester conjugate of claim 19 having the following structure:

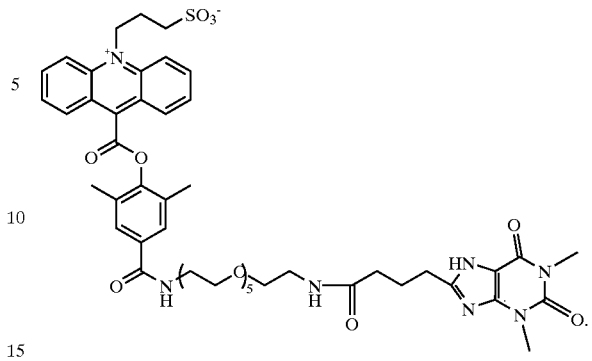

21. The further acridinium ester conjugate of claim 19 having the following structure:

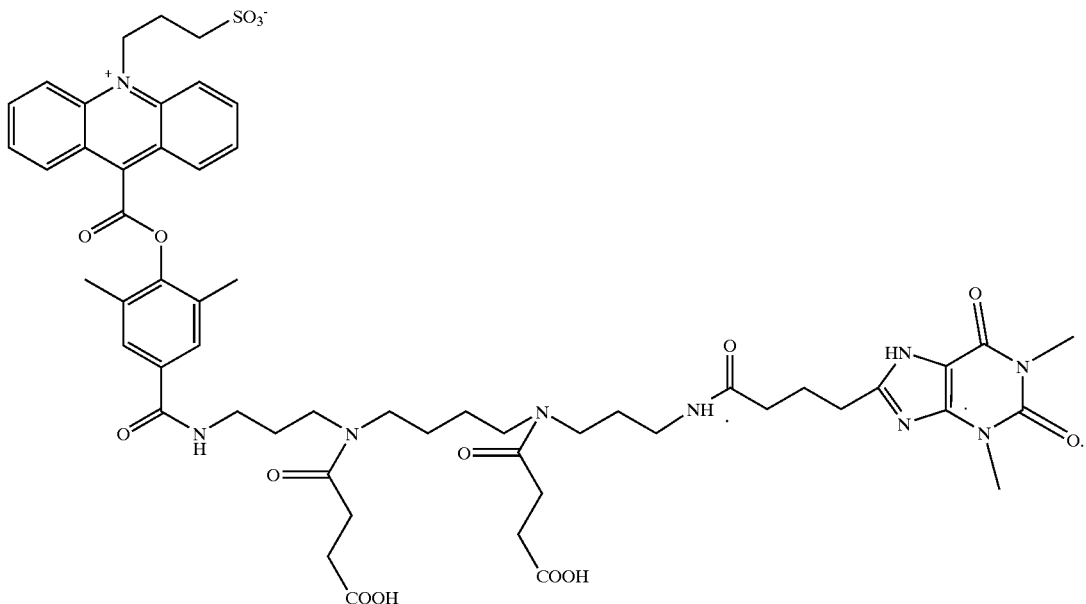

22. A process for performing a competitive assay comprising:
   (a) exposing a sample suspected of containing a target analyte to the acridinium conjugate of claim 3 and to a corresponding binding partner for the target analyte;
   (b) determining the extent to which the conjugate is competitively prevented and/or displaced by target analyte from the sample from forming a binding interaction with the corresponding binding partner;
   (c) correlating the determination made in step (b) above with the presence or amount of target analyte in the sample.

23. A process for performing a sandwich assay comprising:
   (a) exposing a sample suspected of containing a target analyte to the acridinium conjugate of claim 2 and to a corresponding binding partner for the target analyte, wherein said acridinium conjugate and said binding partner are capable of binding to different regions of the same target analyte to form a sandwich;
   (b) initiating the chemiluminescent reaction to evolve detectable light from the sandwich;
   (c) measuring the amount of light detected from the sandwich;
   (d) correlating the amount of the detected light with the presence or amount of target analyte in the sample.

24. A method for improving the hydrophilic properties of a conjugate having the general structure A—B—C, wherein,
   A is an analyte;
   B is a hydrophilic modifier selected from the group consisting of polyethylene glycol having a molecular weight of about 280–5000, or a polyionic spacer derived from a polyamine where the internal, but not necessarily all the amines have been modified by hydrophilic molecules; and
   C is a chemiluminescent acridinium compound containing a phenyl moiety with an ester linkage, comprising conjugating and introducing the hydrophilic modifier onto the phenyl moiety in a position meta or para to the ester linkage to improve the hydrophilic properties.

25. A method for improving the hydrophilic properties of acridinium ester conjugates with the following structure:

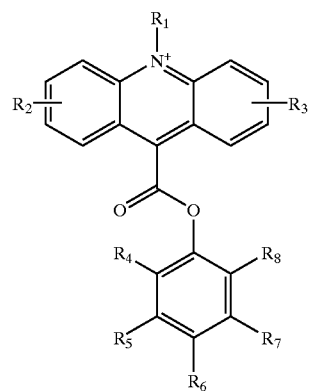

wherein $R_1$ is alkyl, alkyenyl, alkynyl, aryl, sulfoethyl, sulfopropyl, sulfobutyl, or aralkyl having up to 24 carbons and up to 20 heteroatoms selected from the group consisting of nitrogen, oxygen, phosphorus and sulfur;

$R_2$, $R_3$, $R_5$, $R_7$ are hydrogen, amino, hydroxyl, halide, nitro, —CN, $SO_3H$, —SCN, —OR, NHCOR, —COR, —COOR, or —CONHR, wherein R is alkyl, alkenyl, alkynyl, aryl, aralkyl, having up to 24 carbons and up to 20 heteroatoms selected from the group consisting of nitrogen, oxygen, phosphorus and sulfur;

$R_4$ and $R_8$ are alkyl, alkenyl, alkynyl, aralkyl or alkoxyl having up to 8 carbons;

$R_6$=R—L—S—$R_{10}$, wherein $R_6$ has greater than 5 heteroatoms and is alternatively attached on a position of the phenoxy ring which is meta to the ester linkage such that $R_5$ or $R_7$ is attached para to the ester linkage;

R is optionally alkyl, alkenyl, alkynyl, aryl, aralkyl, having up to 24 carbons and up to 20 heteroatoms selected from the group consisting of nitrogen, oxygen, phosphorus and sulfur;

L is selected from the group consisting of ether, thioether, amide, ester and carbamate;

S is selected from the group consisting of polyethylene glycol varying from 280 to 5000 molecular weight and the following structures:

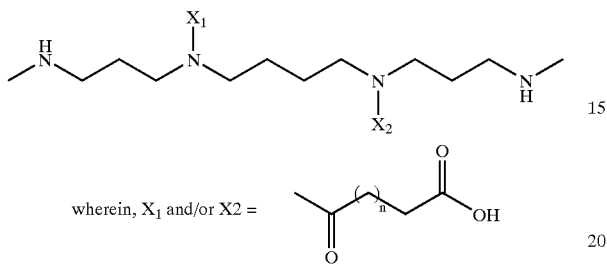

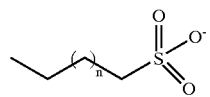

and n = 1,2;

and $R_{10}$ is an electrophile, a leaving group, or a nucleophile, said method comprising conjugating and introducing S onto the phenoxy ring in a position meta or para to the ester linkage to improve the hydrophilic properties.

* * * * *